US008298823B2

(12) United States Patent
Warren et al.

(10) Patent No.: US 8,298,823 B2
(45) Date of Patent: *Oct. 30, 2012

(54) METHODS FOR ANTIBODY PRODUCTION

(75) Inventors: William L. Warren, Orlando, FL (US); Robert Parkhill, Orlando, FL (US); Michael N. Nguyen, Orlando, FL (US); Guzman Sanchez-Schmitz, Orlando, FL (US); Heather Fahlenkamp, Cleveland, OK (US); Russell Higbee, Orlando, FL (US); Donald Drake, III, Orlando, FL (US); Anatoly Kachurin, Orlando, FL (US); David Moe, Orlando, FL (US)

(73) Assignee: Sanofi Pasteur Vaxdesign Corporation, Orlando, FL (US)

( * ) Notice: Subject to any disclaimer, the term of this patent is extended or adjusted under 35 U.S.C. 154(b) by 276 days.

This patent is subject to a terminal disclaimer.

(21) Appl. No.: 12/730,899

(22) Filed: Mar. 24, 2010

(65) Prior Publication Data
US 2010/0178676 A1  Jul. 15, 2010

Related U.S. Application Data

(63) Continuation of application No. 11/375,033, filed on Mar. 15, 2006, now Pat. No. 7,785,883, which is a continuation-in-part of application No. 11/116,234, filed on Apr. 28, 2005, now Pat. No. 7,855,074.

(60) Provisional application No. 60/565,846, filed on Apr. 28, 2004, provisional application No. 60/643,175, filed on Jan. 13, 2005.

(51) Int. Cl.
*C12N 5/16* (2006.01)
*C12N 5/02* (2006.01)

(52) U.S. Cl. ............................ 435/326; 435/375; 435/377

(58) Field of Classification Search ........................ None
See application file for complete search history.

(56) References Cited

U.S. PATENT DOCUMENTS

| | | | |
|---|---|---|---|
| 5,008,116 A | 4/1991 | Cahn | |
| 5,160,490 A | 11/1992 | Naughton et al. | |
| 5,354,686 A | 10/1994 | Haberman | |
| 5,562,910 A | 10/1996 | Daynes et al. | |
| 5,725,856 A | 3/1998 | Hudziak et al. | |
| 5,739,001 A | 4/1998 | Brown et al. | |
| 5,750,329 A | 5/1998 | Quinn et al. | |
| 6,177,282 B1 | 1/2001 | McIntyre | |
| 6,274,378 B1 | 8/2001 | Steinman et al. | |
| 6,479,064 B1 | 11/2002 | Atala | |
| 6,541,225 B1 | 4/2003 | Li | |
| 6,835,550 B1 | 12/2004 | Estell et al. | |
| 8,003,385 B2 * | 8/2011 | Sukumar et al. ............ 435/326 |
| 2002/0155108 A1 | 10/2002 | Barbera-Guillem et al. | |
| 2003/0109042 A1 | 6/2003 | Wu et al. | |
| 2003/0147923 A1 | 8/2003 | Klaviniskis | |
| 2003/0199006 A1 | 10/2003 | Britz et al. | |
| 2003/0207287 A1 | 11/2003 | Short | |
| 2004/0009943 A1 | 1/2004 | Semple et al. | |
| 2004/0109876 A1 | 6/2004 | Yamamoto et al. | |
| 2004/0234510 A1 | 11/2004 | Mochitate | |
| 2005/0191743 A1 | 9/2005 | Wu et al. | |
| 2005/0229264 A1 | 10/2005 | Chang et al. | |
| 2005/0282148 A1 | 12/2005 | Warren et al. | |
| 2006/0078540 A1 | 4/2006 | Warren et al. | |
| 2006/0105454 A1 | 5/2006 | Son et al. ........................ 435/325 |
| 2006/0270029 A1 | 11/2006 | Warren et al. | |
| 2006/0275270 A1 | 12/2006 | Warren et al. | |
| 2007/0015136 A1 | 1/2007 | Sanchez-Schmitz et al. | |
| 2007/0141552 A1 | 6/2007 | Warren et al. | |
| 2007/0154956 A1 | 7/2007 | Warren et al. | |
| 2007/0178076 A1 | 8/2007 | Drake et al. | |
| 2007/0218054 A1 | 9/2007 | Sukumar et al. | |
| 2008/0008653 A1 | 1/2008 | Tew et al. | |
| 2009/0011455 A1 | 1/2009 | Warren et al. | |
| 2009/0104221 A1 | 4/2009 | El Shikh et al. | |
| 2009/0117581 A1 | 5/2009 | Warren et al. | |
| 2011/0171689 A1 * | 7/2011 | Warren et al. ................ 435/70.4 |

FOREIGN PATENT DOCUMENTS

| | | |
|---|---|---|
| EP | 0358506 | 9/1989 |
| EP | 1013668 A1 | 6/2000 |
| EP | 1437147 | 9/2002 |
| EP | 1970444 | 12/2006 |
| WO | 99/12972 | 3/1999 |
| WO | WO 99/15629 | 4/1999 |
| WO | WO 99/43788 | 9/1999 |
| WO | WO 99/49319 | 9/1999 |
| WO | WO 03/041568 | 5/2003 |
| WO | WO 03/050271 | 6/2003 |
| WO | WO 2004/031361 | 4/2004 |

(Continued)

OTHER PUBLICATIONS

Takeuchi et al., CCL21 Chemokine Regulates Chemokine Receptor CCR7 Bearing Malignant Melanoma Cells, Clin. Cancer Res. 10:2351-2358 (2004).
Katakai et al., Lymph Node Fibroblastic Reticular Cells Construct the Stromal Reticulum via Contact with Lymphocytes, J. Exp. Med. 200(6):783-795 (2004).
Caux et al., Functional CD40 on B Lymphocytes and Dendritic Cells, Res. Immunol. 145:235-239 (1994).
Inaba et al., Clustering of Dendritic Cells, Helper T Lymphocytes, and Histocompatible B Cells During Primary Antibody Response in vitro, J. Exp. Med. 160:858-876 (1984).
Grouard et al., Regulation of Human B Cell Activation by Follicular Dendritic Cell and T Cell Signals, Curr. Topic Microbiol. Immunol. 201:105-117 (1995).
Ansel, et al., "A Chemokine-Driven Positive Feedback Loop Organizes Lymphoid Follicles", Nature, vol. 406, pp. 309-314 (2000).

(Continued)

Primary Examiner — Michail Belyavskyi
(74) Attorney, Agent, or Firm — Roylance, Abrams, Berdo & Goodman, L.L.P.

(57) ABSTRACT

The present invention relates to methods of constructing an integrated artificial immune system that comprises appropriate in vitro cellular and tissue constructs or their equivalents to mimic the normal tissues that interact with vaccines in mammals. The artificial immune system can be used to test the efficacy of vaccine candidates in vitro and thus, is useful to accelerate vaccine development and testing drug and chemical interactions with the immune system.

34 Claims, 30 Drawing Sheets

FOREIGN PATENT DOCUMENTS

| WO | WO 2004/101773 | 11/2004 |
|---|---|---|
| WO | 2005/013896 | 2/2005 |
| WO | 2005/072088 | 8/2005 |
| WO | WO 2005/104755 | 11/2005 |
| WO | WO 2007/075979 | 7/2007 |
| WO | 2007/108835 | 9/2007 |
| WO | WO 2007/106559 | 9/2007 |
| WO | WO 2007/146267 | 12/2007 |

OTHER PUBLICATIONS

Aydar et al. (2005) *J. Immunol.* 174, 5358-5366.
Badylak, S.F. et al., "*Small Intestinal Submucosa: A Substrate for in vitro Cell Growth*," J. Biomater. Sci. Polymer Edn. (1998), vol. 9, No. 8, pp. 863-878.
Bai et al., "*Generation of Dendritic Cells From Human Bone Marrow Mononuclear Cells: Advantages From Clinical Applications in Comparison to Peripheral Blood Monocyte Derived Cells,*" International Journal of Oncology, (2002), 20(2), pp. 247-253.
Banchereau, et al., "Dendritic Cells and the Control of Immunity", Nature, vol. 392, pp. 245-252 (1998).
Banchereau, et al., "Immunobiology of Dendritic Cells", Annu. Rev. Immunol., vol. 18, pp. 767-811 (2000).
Baumgarth, "A Two-Phase Model of B-Cell Activation", Immunological Review, vol. 176, pp. 171-180 (2000).
Benbrook et al., "Organotypic cultures represent tumor microenvironment for drug testing," Drug Discovery Today: Disease Models, 3(2), pp. 143-148 (2005).
Berman, et al., "Roles of Platelet/Endothelial Cell Adhesion Molecule-1 (PECAM-1, CD31) in Natural Killer Cell Transendothelial Migration and Beta 2 Integrin Activation", The Journal of Immunology, vol. 156, pp. 1515-1524 (1996).
Birkness et al., A Tissue Culture Bilayer Model to Study the Passage of Neisseria Meningitidis, *Infection and Immunity*, Feb. 1995, p. 402-409, vol. 63, No. 2.
Birkness et al., An in Vitro Tissue Culture Bilayer Model to Examine Early Events in Mycobacterium Tuberculosis Infection, *Infection and Immunity*, Feb. 1999, p. 653-658, vol. 67, No. 2.
Bogdan, et al., "Fibroblasts as Host Cells in Latent Leishmaniosis", J. Exp. Med., vol. 191, pp. 2121-2129 (2000).
Boni et al. (2006) *Eur. J. Immunol.* 36, 3157-3166.
Brandtzaeg, P. et al., "*Mucosal B Cells: Phenotypic Characteristics, Transcriptional, Regulation, and Homing Properties,*" Immunological Reviews (2005), vol. 206, pp. 32-63.
Bromelow, K. V. et al., "*Whole Blood Assay for Assessment of the Mixed Lymphocyte Reaction,*" Journal of Immunological Methods, (2001), 247(1-2), pp. 1-8.
Büchele, S. et al., "*Presentation of Tetanus Toxoid to Autologous T Cells by Dendritic Cells Generated From Human Blood. Improved Specificity With Dendritic Cells Generated Without Fetal Calf Serum,*" Advances in Experimental Medicine and Biology, (1997), vol. 417, pp. 233-237.
Buchler et al. (2003) *Vaccine*, 21, 877-882.
Butcher, et al., "Lymphocyte Trafficking and Regional Immunity", Advances in Immunology, vol. 72, pp. 209-253 (1999).
Castro, et al., "Spleen-Derived Stromal Cells. Adhesion Molecules Expression and Lymphocyte Adhesion to Reticular Cells", Eur. J. Cell. Biol., vol. 74, 321-328 (1997).
Caux et al. (1995) *J. Immunol.* 155, 5427-5435.
Cayeux et al. (1999) *Eur. J. Immunol.* 29, 225-234.
Chen, et al., "A Film Tension Theory of Phagocytosis", Journal of Colloid and Interface Science, vol. 190, pp. 118-133 (1997).
Chou, et al., "The Detection of the HLA-B27 Antigen by Immunomagnetic Separation and Enzyme-Linked Immunosorbent Assay-Comparison with a Flow Cytometric Procedure", Journal of Immunological Methods, vol. 255, pp. 15-22 (2001).
Clayton et al., Clin. Exp. Immunol., 2003, v.132, p. 174-179.
Crivellato, et al., "Stromal Cell Organisation in the Mouse Lymph Node. A Light and Electron Microscopic Investigation Using the Zinc Iodide-Osmium Technique", J. Anat., vol. 190, pp. 85-92 (1997).

Cyster, "Chemokines and the Homing of Dendritic Cells to the T Cell Areas of Lymphoid Organs", J. Exp. Med. Volume 189, No. 3, pp. 447-450 (1999).
Cyster, et al., "Follicular Stromal Cells and Lymphocyte Homing to Follicles", Immunological Reviews, vol. 176, pp. 181-193 (2000).
D'Amico et al., Blood 92:207-214 (1998).
Danke, et al., "HLA Class II-Restricted CD4+ T Cell Responses Directed Against Influenza Viral Antigens Postinfluenza Vaccination", The Journal of Immunology, vol. 171, pp. 3163-3169 (2003).
Denkbas, et al., "Magnetic Chotosan Microspheres: Preparation and Characterization", Reactive & Functional Polymers, vol. 50, pp. 225-232 (2002).
Dubey et al. (2005) *J. Clin. Endocrin & Met.*, 90, 247-255.
Dubois, et al., "Dendritic Cells Enhance Growth and Differentiation of CD40-Activated B Lymphocytes", J. Exp. Med., vol. 185, pp. 941-951 (1997).
Dubois et al., J. Leukocyte Biology, 1999, v.66, p. 224-230.
Edelman et al, A Cultureal Renaissance: in Vitro Cell Biology Embraces Three-Dimensional Context. Exp Neurol. 2005, vol. 192, pp. 1-6.
El Shikh, M. et al., "*Follicular Dendritic Cells Stimulated by Collagen Type I Develop Dendrites and Networks in Vitro,*" Cell and Tissue Research, (2007), 329(1), pp. 81-89.
Forster, et al., "CCR7 Coordinates the Primary Immune Response by Establishing Functional Microenvironments in Secondary Lymphoid Organs", Cell., vol. 99, pp. 23-33 (1999).
Fransson, et al., "Culture of Human Epidermal Langerhans Cells in a Skin Equivalent", British Journal of Dermatology, vol. 139, pp. 598-604 (1998).
Friedl, et al., "CD4+ T Lymphocytes Migrating in Three-Dimensional Collagen Lattices Lack Focal Adhesions and Utilize Beta 1 Integrin-Independent Strategies for Polarization, Interaction with Collagen Fibers and Locomotion", Eur. J. Immunol., vol. 28, pp. 2331-2343 (1998).
Fulcher, et al., "B-Cell Activation Versus Tolerance—The Central Role of Immunoglobulin Receptor Engagement and T-Cell Help", Int. Rev. Immunol., vol. 15, pp. 33-52 (1997).
Furie, et al., "Migration of Neutrophils Across Endothelial Monolayers is Stimulated by Treatment of the Monolayers with Interleukin-1 or Tumor Necrosis Factor-Alpha", The Journal of Immunology, vol. 143, pp. 3309-3317 (1989).
Furuyama, A. et al., "*Assembly of Basement Membrane in vitro by Cooperation Between Alveolar Epithelial Cells and Pulmonary Fibroblasts,*" Cell Structure and Function (1997), vol. 22, pp. 603-614.
Galibert, et al., "CD40 and B Cell Antigen Receptor Dual Triggering of Resting B Lymphocytes Turns on a Partial Germinal Center Phenotype", J. Exp. Med., vol. 183, pp. 77-85 (1996).
Gansuvd et al., Human Immunol., 2003, v.64, p. 427-439.
Garside, et al., "Visualization of Specific B and T Lumphocyte Interactions in the Lymph Node", Science, vol. 281, pp. 96-99 (1998).
Gergel, et al., "Activation of Endothelium by *Borrelia burgdorferi* in Vitro Enhances Transmigration of Specific Subsets of T Lymphocytes", Infection and Immunity, vol. 69, pp. 2190-2197 (2001).
Gretz, et al., "Cords, Channels, Corridors and Conduits: Critical Architectural Elements Facilitating Cell Interactions in the Lymph Node Cortex", Immunological Reviews, vol. 156, pp. 11-24 (1997).
Gretz, et al., "Lymph-borne Chemokines and Other Low Molecular Weight Molecules Reach High Endothelial Venules Via Specialized Conduits While a Functional Barrier Limits Access to the Lymphocyte Microenvironments in Lymph Node Cortex", The Journal of Experimental Medicine, vol. 192, pp. 1425-1439 (2000).
Gretz, et al., "Sophisticated Strategies for Information Encounter in the Lymph Node: The Reticular Network as a Conduit of Soluble Information and a Highway for Cell Traffic", The Journal of Immunology, vol. 157, pp. 495-499 (1996).
Gundersen, et al., "Magnetic Bead Antigen Capture Enzyme-Linked Immunoassay in Microtitre Trays for Rapid Detection of Schistosomal Circulating Anodic Antigen", Journal of Immunological Methods, vol. 148, pp. 1-8 (1992).

Gunn, et al., "Mice Lacking Expression of Secondary Lymphoid Organ Chemokine Have Defects in Lymphocyte Homing and Dendritic Cell Localization", J. Exp. Med., vol. 189, pp. 451-460 (1999).

Gunzer, et al., "Antigen Presentation in Extracellular Matrix: Interactions of T Cells with Dendritic Cells are Dynamic, Short Lived, and Sequential", Immunity, vol. 13, pp. 323-332 (2000).

Hasbold, et al., "Quantitative Analysis of Lymphocyte Differentiation and Proliferation in Vitro Using CarboxyFluorescein Diacetate Succinimidyl Ester", Immunology and Cell Biology, vol. 77, pp. 516-522 (1999).

Irvine, et al., "Nanoscale Clustering of RGD Peptides at Surfaces Using Comb Polymers. 1. Synthesis and Characterization of Comb Thin Films", Biomacromolecules, vol. 2, pp. 85-94 (2001).

Jenkins, et al., "In Vivo Activation of Antigen-Specific CD4 T Cells", Annu. Rev. Immunol., vol. 19, pp. 23-45 (2001).

Junt, et al., "Antiviral Immune Responses in the Absence of Organized Lymphoid T Cell Zones in plt/plt Mice", The Journal of Immunology, vol. 168, pp. 6032-6040 (2002).

Kabashima, et al., "Prostaglandin $E_2$-EP4 Signaling Initiates Skin Immune Responses by Promoting Migration and Maturation of Langerhans Cells", Nature Medicine, vol. 9, pp. 744-749 (2003).

Kadowaki, et al., "Subsets of Human Dendritic Cell Precursors Express Different Toll-Like Receptors and Respond to Different Microbial Antigens", J. Exp. Med. Volume 194, No. 6, pp. 863-869 (2001).

Kaldjian, et al., "Spatial and Molecular Organization of Lymph Node T Cell Cortex: A Labyrinthine Cavity Bounded by an Epithelium-Like Monolayer of Fibroblastic Reticular Cells Anchored to Basement Membrane-like Extracellular Matrix", International Immunology, vol. 13, pp. 1243-1253 (2001).

Khademhosseini et al., "Microscale Technologies for Tissue Engineering and Biology," Proc. Natl. Acad. Sci. USA, vol. 103, pp. 2480-2487 (2006).

Kim et al., "*Three-Dimensional Tissue Culture Models in Cancer Biology*," Seminars in Cancer Biology, (2005), 15(5), pp. 365-377.

Kim, H.-J. et al, Establishment of Early Lymphoid Organ Infrastructure in Transplanted Tumors Mediated by Local Production of Lymphotoxin α and in Combined Absence of Functional B and T Cells. In J. of Immunology, vol. 172:4037-4047 (2004).

Kosco, M. H. et al., "*Folicular Dendritic Cell-Dependent B-Cell Proliferation and in Vitro Germinal Center*," Lymphatic Tissues in Vivo Immune Responses, (1991), pp. 687-690.

Kosco, M. H. et al., "*Follicular Dendritic Cell-Dependent Adhesion and Proliferation of B Cells in Vitro*," Journal of Immunology, (1992), 148(8), pp. 2331-2339.

Kosco, M. H. et al., "*Follicular Dendritic Cells and Germinal Center Formation In-Vitro*," Accessory Cells in HIV and Other Retroviral Infections: Morphological and Functional Aspects; Workshop on Morphological and Functional Aspects of Accessory Cells in retroviral Infections, Hamberg, Germany, 23-24, p. 44-49 (1991).

Kosco-Vilbois, "Are Follicular Dendritic Cells Really Good for Nothing", Nature Reviews Immunology, vol. 3, pp. 764-769 (2003).

Kourilov, et al., "Magnetic-Bead Enzyme-Linked Immunosorbent Assay Verifies Adsorption of Ligand and Epitope Accessibility", Analytical Biochemistry, vol. 311, pp. 166-170 (2002).

Larsson, et al., "Requirement of Mature Dendritic Cells for Efficient Activation of Influenza A-Specific Memory CD8 + T Cells", The Journal of Immunology, vol. 165, pp. 1182-1190 (2000).

LeBedis, et al., "Peripheral Lymph Node Stromal Cells Can Promote Growth and Tumorigenicity of Breast Carcinoma Cells Through the Release of IGF-I and EGF", Int. J. Cancer, vol. 100, pp. 2-8 (2002).

Levenberg, S. et al., "*Advances in Tissue Engineering*," Current Topics in Developmental Biology, (2004), vol. 61, pp. 113-134.

Luk, et al., "Rapid and Sensitive Detection of *Salmonella* (O:6,7) by Immunomagnetic Monoclonal Antibody-Based Assays", Journal of Immunological Methods, vol. 137, pp. 1-8 (1991).

Lukas, et al., "Human Cutaneous Dendritic Cells Migrate Through Dermal Lymphatic Vessels in a Skin Organ Culture Model", The Journal of Investigative Dermatology, vol. 106, pp. 1293-1299 (1996).

Manna, P. et al., "Differentiation and Functional Maturation of Human CD14<+> Adherent Peripheral Blood Monocytes by Xenogeneic Endothelial Cells: Up-Regulation of Costimulation Cytokine Generation, and Toll-Like Receptors," Transplantation, (2002), 74(2), pp. 243-252.

Matsumoto, et al., "Affinity Maturation Without Germinal Centres in Lymphotoxin-α-Deficient Mice", Nature, vol. 382, pp. 462-466 (1996).

Mebius, "Organogenesis of Lymphoid Tissues", Nat. Rev. Immunol, vol. 3, pp. 292-303 (2003).

Mellman, et al., "Dendritic Cells: Specialized and Regulated Antigen Processing Machines", Cell, vol. 106, pp. 255-258 (2001).

Miller, et al., "Two-Photon Imaging of Lymphocyte Motility and Antigen Response in Intact Lymph Node", Science, vol. 296, pp. 1869-1873 (2002).

Mori, et al., "Mice Lacking Expression of the Chemokines CCL21-ser and CCL19 (plt Mice) Demonstrate Delayed but Enhanced T Cell Immune Responses", J. Exp. Med., vol. 193, No. 2, pp. 207-217 (2001).

Moser et al. (2000) Nature Immunol. 1, 199-205.

Nakamura, M. et al., "*Expression of Leptin in Two-layered Culture of Gastric Mucous Cells and Fibroblasts: Effect of Helicobacter pylori Attachment*," Aliment Pharmacol Ther. (2004), vol. 20, suppl. 1, pp. 125-130.

Nakatsu, M. N. et al., "*Angiogenic Sprouting and Capillary Lumen Formation Modeled by Human Umbilical Vein Endothelial Cells (HUVEC) in Fibrin Gels: The Role of Fibroblasts and Angiopoietin-1*," Microvascular Research (2003), vol. 66, pp. 102-112.

Neves, A. R. et al., "*Dendritic Cells Derived From Metastatic Cancer Vaccinated With Allogeneic Dendritic Cell-Autologous Tumor Cell Hybrids Express More CD86 and Induce Higher Levels of Interferon-Gamma in Mixed Lymphocyte Reactions*," Cancer Immunology and Immunotherapy, (2005), 54(1), pp. 61-66.

Oehler et al. (2000) *Ann. Hematol.*, 79, 355-362.

Okamoto et al, Artificial Lymph Nodes Induce Potent Secondary Immune Response in Naïve and Immunodeficient Mice. J. Clin. Invest. Apr. 2007, vol. 117, No. 4, pp. 997-1007.

Parker, "T Cell-Dependent B Cell Activation", Annu. Rev. Immunol., vol. 11, pp. 331-360 (1993).

Pasparakis, et al., "Immune and Inflammatory Responses in TNFα Deficient Mice: A Critical Requirement for TNFα in the Formation of Primary B Cell Follicles, Follicular Dendritic Cell Networks and Germinal Centers, and in the Maturation of the Humoral Immune Response", J. Exp. Med., vol. 184, pp. 1397-1411 (1996).

Phillips, et al., "Activation of Pertussis Toxin-Sensitive CXCL12 (SDF-1) Receptors Mediates Transendothelial Migration of T Lymphocytes Across Lymph Node High Endothelial Cells", Eur. J. Immunol., vol. 32, pp. 837-847 (2002).

Podgrabinska, et al., "Molecular Characterization of Lymphatic Endothelial Cells", Proc. Natl. Acad. Sci. U.S.A., vol. 99, No. 25, pp. 16069-16074 (2002).

Portner, R et al, Chapter 2: An Overview on Bioreactor Design, Prototyping, and Process Control for Reproducible Three-Dimensional Tissue Culture. In Drug Testing in Vitro: Breakthrough Cell Cultur Technology. Eds. U. Marx and V. Sandig 2006: Wiley-VCH, pp. 65-69.

Poznansky, et al., "Efficient Generation of Human T Cells From a Tissue-Engineered Thymic Organoid", Nature Biotechnology, vol. 18, pp. 729-734 (2000).

Qu, et al., "Autocrine Type I IFN and Contact with Endothelium Promote the Presentation of Influenza A Virus by Monocyte-Derived APC", The Journal of Immunology, vol. 170, pp. 1010-1018 (2003).

Randolph, et al., "A Physiologic Function for p-Glycoprotein (MDR-1) During the Migration of Dendritic Cells from Skin Via Afferent Lymphatic Vessels", Proc. Natl. Acad. Sci., vol. 95, pp. 6924-2929 (1998).

Randolph, et al., "A Soluble Gradient of Endogenous Monocyte Chemoattractant Protein-1 Promotes the Transendothelial Migration of Monocytes in Vitro", The Journal of Immunology, vol. 155, pp. 3610-3618 (1995).

Randolph, et al., "Differentiation of Monocytes into Dendritic Cells in a Model of Transendothelial Trafficking", Science, vol. 282, pp. 480-483 (1998).

Randolph, et al., "Mononuclear Phagocytes Egress from an in Vitro Model of the Vascular Wall by Migrating Across Endothelium in the Basal to Apical Direction: Role of Intercellular Adhesion Molecule 1 and the CD11/CD18 Integrins", J. Exp. Med., vol. 183, pp. 451-462 (1996).

Randolph, et al., "Role of Tissue Factor in Adhesion of Mononuclear Phagocytes to and Trafficking Through Endothelium in Vitro", Blood, vol. 92, pp. 4167-4177 (1998).

Randolph, et al., "The CD16(+) (FcγRIII(+)) Subset of Human Monocytes Preferentially Becomes Migratory Dendritic Cells in a Model Tissue Setting", J. Exp. Med., vol. 196, No. 4, pp. 517-527 (2002).

Razanajaona, et al., In Vitro Triggering of Somatic Mutation in Human Naïve B Cells, The Journal of Immunology, vol. 159, pp. 3347-3353 (1997).

Regnier, et al., "Integration of Langerhans Cells into a Pigmented Reconstructed Human Epidermis", The Journal of Investigative Dermatology, vol. 109, No. 4, pp. 510-512 (1997).

Robbiani, et al., "The Leukotriene C4 Transporter MRP1 Regulates CCL19 (MIP-3β, ELC)-Dependent Mobilization of Dendritic Cells to Lymph Nodes", Cell, vol. 103, pp. 757-768 (2000).

Roos et al. (2005) *Expert Opin. Drug Metab. Toxicol.* 1, 187-202.

Rot, "In Situ Binding Assay for Studying Chemokine Interactions with Endothelial Cells", Journal of Immunological Methods, vol. 273, pp. 63-71 (2003).

Ruco, et al., "Expression and Cell Distribution of the Intercellular Adhesion Molecule, Vascular Cell Adhesion Molecule, Endothelial Leukocyte Adhesion Molecule, and Endothelial Cell Adhesion Molecule (CD31) in Reactive Human Lymph Nodes and in Hodgkin's Disease", American Journal of Pathology, vol. 140, pp. 1337-1344 (1992).

Safarik, et al., "Use of Magnetic Techniques for the Isolation of Cells", Journal of Chromatography B, vol. 722, pp. 33-53 (1999).

Santini et al. (2000) *J. Exp. Med.* 191, 1777-1788.

Sarradell et al. (2003) *Vet. Pathol.*, 40, 395-404.

Seguin, R. et al., "*Human Brain Endothelial Cells Supply Support for Monocyte Immunoregulartory Functions,*" Journal of Neuroimmunology, (2003), 135(1-2), pp. 96-106.

Sieben, et al., "Comparison of Different Particles and Methods for Magnetic Isolation of Circulating Tumor Cells", Journal of Magnetism and Magnetic Materials, vol. 225, pp. 175-179 (2001).

Simmingskoeld et al., Scand. J. Immunol. 7:233-238 (1978).

Skibinski, et al., "Enhancement of Terminal B Lymphocyte Differentiation in Vitro by Fibroblast-Like Stromal Cells from Human Spleen", Eur. J. Immunol., vol. 28, pp. 3940-3948 (1998).

Skibinski, et al., "The Role of Hepatocyte Growth Factor and Its Receptor c-met in Interactions Between Lymphocytes and Stromal Cells in Secondary Human Lymphoid Organs", Immunology, vol. 102, pp. 506-514 (2001).

Soderberg, O. et al., "*The Human Follicular Dendritic Cell Line FDC-1 Binds Immune Complexes and Promotes Somatic Hypermutation,*" Blood, (2001), 98(11 part 2), pp. 40b.

Sprent, et al., "Antigen-Induced Selective Recruitment of Circulating Lymphocytes", Cellular Immunology, vol. 2, pp. 171-181 (1971).

Stoll, et al., "Dynamic Imaging of T Cell-Dendritic Cell Interactions in Lymph Nodes", Science, vol. 296, pp. 1873-1876 (2002).

Stuart, et al., "The Human Reticular Cell: Morphology and Cytochemistry", J. Pathol, vol. 103, pp. 41-47 (1971).

Suematsu, et al., "Generation of a Synthetic Lymphoid Tissue-Like Organoid in Mice", Nature Biotechnology, vol. 22, No. 12, pp. 1539-1545 (Dec. 2004).

Tan et al. (2005) *J. Leuk. Biol.* 78, 319-324.

Tarte et al., Leukemia, vol. 14, 2000, abstract p. 2182.

Tew et al. (2001) *Trends Immunol.* 22, 361-367.

Tew, J. G. et al., "*Follicular Dendritic Cells as Accessory Cells,*" Immunological Reviews, (1990), No. 117, pp. 185-211.

Warren, W., The Front-End of Vaccine Manufacturing: Getting Good Candidates from the Get-Go. Workshop on Science and Technology in North American Rapid Vaccine Manufacturing, Jan. 26, 2007.

Hashimoto, K., et al., Direct Observation and Analysis of Spatiotemporal Dynamics of Individual Living Monocyte During Transendothelial Migration. Atherosclerosis 177(1):19-27 (Nov. 2004).

Hashimoto, K., et al., Direct Observation and Analysis of Spatiotemporal Dynamics of Individual Living Monocyte During Transendothelial Migration. Collection of Papers from 16th Bioengineering Conference, Jan. 21, 2004, pp. 13-14.

Higbee, R., et al., An Immunologic Model for Rapid Vaccine Assessment—A Clinical Trial in a Test Tube. ALTA 37, Suppl. 1, 19-27 (2009).

Giese, C. et al., A human lymph node in vitro—challenges and progress, Artificial Organs, 30(10):803-808 (2006).

Giese, C. et al., Immunological substance testing on human lymphatic micro-organoids in vitro, Journal of Biotechnology, 148:38-45 (2010).

Tew, J.G. et al., "*Follicular Dendritic Cells and Presentation of Antigen and Costimulatory Signals to B Cells,*" Immunological Reviews (1997), vol. 156, pp. 39-52.

Thompson, H.G. et al., "*A Three-dimensional in vitro Model of Angiogenesis in the Airway Mucosa,*" Pulmonary Pharmacology & Therapeutics (2007), vol. 20, pp. 141-148.

Toyama, et al., "Memory B Cells Without Somatic Hypermutation are Generated from Bcl 6 Deficient B Cells", Immunity, vol. 17, pp. 329-339 (2002).

Transwell® Permeable Supports Selection and Use Guide, Corning Corp., pp. 1-12 (2009).

Tsunoda, R. et al., "*Follicular Dendritic Cells in Vitro Modulate the Expression of Fas and Bcl-2 on Germinal Center B Cells,*" Cell and Tissue Research, (2000), 299(3), pp. 395-402.

Tsunoda, R. et al., "*Human Follicular Dendritic Cells in Vitro and Follicular Dendritic-Cell-Like Cells,*" Cell and Tissue Research, (1997), 288(2), pp. 381-389.

Van Den Berg, et al., "Localization of β 1 Integrins and Their Extracellular Ligands in Human Lymphoid Tissues", American Journal of Pathology, vol. 143, pp. 1098-1110 (1993).

Weppler et al., Modulation of Endotoxin-Induced Neutrophil Transendothelial Migration by Alveolar Epithelium in a Defined Bilayer Model, *Experimental Lung Research* 32:10, 455-482 (2006).

West, et al., "Polymeric Biomaterials with Degradation Sites for Proteases Involved in Cell Migration", Macromolecules, vol. 32, pp. 241-244 (1999).

Wu et al. (2008) *J. Immunol.* 180, 281-290.

Wu, Y. et al., "*Influence of Follicular Dendritic Cells and Primed T Cells on Somatic Hypermutation in in Vitro Germinal Centers,*" Journal of Immunology, (2006), 176(suppl. S), pp. S235-S236.

Zhang, S. et al., "*Growth Factors Secreted by Bronchial Epithelial Cells Control Myofibroblast Proliferation: An in vitro Co-culture Model of Airway Remodeling in Asthma,*" Laboratory Investigation (1999), vol. 79, No. 4, pp. 395-405.

International Search Report—PCT/US2007/083795 , 2007.
International Search Report—PCT/US2008/056720, 2008.
International Search Report—PCT/US08/70107a , 2008.
International Search Report—PCT/US06/048959 , 2006.
International Search Report—PCT/US07/014826 , 2007.
International Search Report—PCT/US08/69172 2008.
International Search Report—PCT/US07/013745 , 2007.
International Search Report—PCT/US05/14444 , 2005.
International Search Report—PCT/US06/43563 , 2006.
International Search Report—PCT/US06/43712 , 2006.
International Search Report—PCT/US07/006532, 2007.
International Search Report—PCT/US07/006571 , 2007.
200 I International Search Report—PCT/US07/013871 , 2006.
International Search Report—PCT/US06/049128, 2008.
International Search Report—PCT/US08/70107b , 2010.
Dynal (Norway): http://www.invitrogen.com/, 2010.
2010 Agowa GMBH (Germany): http://agowade/contentsframes/magneticseparation/particle.html, 2010.
http://www.xcyte.com.
Protocol for anti-CD3 Activation of T-Cells from E-Bioscience (San Diego, CA): http://www.ebioscience..com/ebioscience/appls/AC145.htm, 2010.

* cited by examiner

Designer membranes containing Protasan/collagen ECM and covered with HuVEC cells, as a means of incorporating the VS into a bireactor system.

HuVEC cells seeded on the 1st side, incubated for 1 hour then cultured - 1 day

HuVEC cells seeded on 2nd side, incubated for 1 hour then contunued culture.

Side 1

Side 2

Mockup of Digitally Printed Lymph Node (Left) and a Retinal Image of Vasculature (right)

Laminate Microchannel

Microfluidic bioreactor and optical diagnostics on microfluidic backplane

Cross-Sectional View of Direct Deposition in the AIS Device

Fabrication of 3-Layer Planar Waveguide

Laser-machined integrated optical waveguides: $n_1$ represents the refractive index of the waveguide core, $n_2$ is the cladding index

Bioreactor construction with collagen membranes on rings and support matrix (A) Polycarbonate Bioreactor Design (B)

METHODS FOR ANTIBODY PRODUCTION

CROSS-REFERENCE TO RELATED APPLICATIONS

This application is a continuation of U.S. application Ser. No. 11/375,033, filed Mar. 15, 2006, now issued as U.S. Pat. No. 7,785,883, which in turn is a continuation-in-part of U.S. application Ser. No. 11/116,234, filed Apr. 28, 2005, now issued as U.S. Pat. No. 7,855,074, which claims benefit of U.S. Provisional Application Ser. No. 60/565,846, filed Apr. 28, 2004, and U.S. Provisional Application Ser. No. 60/643,175, filed Jan. 13, 2005. U.S. application Ser. No. 11/116,234 also claims benefit of International Application No. PCT/US05/14444, filed Apr. 28, 2005. Each of these applications is hereby incorporated by reference in its entirety.

STATEMENT REGARDING FEDERALLY SPONSORED RESEARCH

This invention was made with government support under contract number NBCHC060058, awarded by the Defense Advanced Research Projects Agency, issued by the U.S. Army Medical Research Acquisition Activity, and administered by the U.S. Department of the Interior-National Business Center. The government has certain rights in the invention.

BACKGROUND OF THE INVENTION

1. Field of The Invention

The present invention is directed to a method for constructing an integrated artificial human tissue construct system and, in particular, construction of an integrated human immune system for in vitro testing of vaccines, adjuvants, immunotherapy candidates, cosmetics, drugs, biologics, and other chemicals. The artificial immune system is useful for assessing the interaction of substances with the immune system, and thus can be used to accelerate and improve the accuracy and predictability of vaccine, drug, biologic, immunotherapy, cosmetic, and chemical development.

2. Background of the Technology

The development and biological testing of human vaccines has traditionally relied on small animal models (e.g., mouse and rabbit models) and then non-human primate models. However, such small animal models are expensive and non-human primate models are both expensive and precious.

The mammalian immune system uses two general adaptive mechanisms to protect the body against environmental pathogens. When a pathogen-derived molecule is encountered, the immune response becomes activated to ensure protection against that pathogenic organism.

The first immune system mechanism is the non-specific (or innate) inflammatory response. The innate immune system appears to recognize specific molecules that are present on pathogens but not on the body itself.

The second immune system mechanism is the specific or acquired (or adaptive) immune response. Innate responses are fundamentally the same for each injury or infection; in contrast, acquired responses are custom-tailored to the pathogen in question. The acquired immune system involves a specific immunoglobulin (antibody) response to many different molecules present in the pathogen, called antigens. In addition, a large repertoire of T cell receptors (TCR) is sampled for their ability to bind processed forms of the antigens bound to major histocompatibility complex (MHC, also known as human leukocyte antigen, HLA) class I and II proteins on the surface of antigen-presenting cells (APCs), such as dendritic cells (DCs).

The immune system recognizes and responds to structural differences between self and non-self proteins. Proteins that the immune system recognizes as non-self are referred to as antigens. Pathogens typically express large numbers of highly complex antigens.

Acquired immunity is mediated by specialized immune cells called B and T lymphocytes (or simply B and T cells). Acquired immunity has specific memory for antigenic structures; repeated exposure to the same antigen increases the response, which increases the level of induced protection against that particular pathogen.

B cells produce and mediate their functions through the actions of antibodies. B cell-dependent immune responses are referred to as "humoral immunity," because antibodies are found in body fluids.

T cell-dependent immune responses are referred to as "cell mediated immunity," because effector activities are mediated directly by the local actions of effector T cells. The local actions of effector T cells are amplified through synergistic interactions between T cells and secondary effector cells, such as activated macrophages. The result is that the pathogen is killed and prevented from causing diseases.

Similar to pathogens, vaccines function by initiating an innate immune response at the vaccination site and activating antigen-specific T and B cells that can give rise to long term memory cells in secondary lymphoid tissues. The precise interactions of the vaccine with cells at the vaccination site and with T and B cells of the lymphoid tissues are important to the ultimate success of the vaccine.

Almost all vaccines to infectious organisms were and continue to be developed through the classical approach of generating an attenuated or inactivated pathogen as the vaccine itself. This approach, however, fails to take advantage of the recent explosion in our mechanistic understanding of immunity. Rather, it remains an empirical approach that consists of making variants of the pathogen and testing them for efficacy in non-human animal models.

Advances in the design, creation and testing of more sophisticated vaccines have been stalled for several reasons. First, only a small number of vaccines can be tested in humans, because, understandably, there is little societal tolerance for harmful side effects in healthy people, especially children, exposed to experimental vaccines. With the exception of cancer vaccine trials, this greatly limits the innovation that can be allowed in the real world of human clinical trials. Second, it remains challenging to predict which epitopes are optimal for induction of immunodominant CD4 and CD8 T cell responses and neutralizing B cell responses. Third, small animal testing, followed by primate trials, has been the mainstay of vaccine development; such approaches are limited by intrinsic differences between human and non-human species, and ethical and cost considerations that restrict the use of non-human primates. Consequently, there is a slow translation of basic knowledge to the clinic, but equally important, a slow advance in the understanding of human immunity in vivo.

The artificial immune system (AIS) of the present invention can be used to address this inability to test many novel vaccines in human trials by instead using human tissues and cells in vitro. The AIS enables rapid vaccine assessment in an in vitro model of human immunity. The AIS provides an additional model for testing vaccines in addition to the currently used animal models.

Attempts have been made in modulating the immune system. See, for example, U.S. Pat. No. 6,835,550 B1, U.S. Pat. No. 5,008,116, Suematsu et al., [*Nat. Biotechnol.*, 22, 1539-1545, (2004)] and U.S. Patent Publication No. 2003/0109042. Nevertheless, none of these publications describe or suggest an artificial immune system, which comprises a vaccine site (VS), lymphoid tissue equivalent (LTE), and the use of an AIS for assessing the interaction of substances with the immune system.

SUMMARY OF THE INVENTION

The present invention provides an integrated system of the functionally equivalent human tissues for testing vaccines, adjuvants, drugs, biologics, cosmetics, and other chemicals in vitro. One aspect of the invention relates to a method for constructing a functionally equivalent tissue using blueprints that design, as opposed to fabricate, morphologically equivalent constructs. Functional equivalency to the human immune system is achieved by building engineered tissue constructs (ETCs), housed in a modular, immunobioreactor system.

Another aspect of the invention relates to a method of constructing an artificial immune system (AIS). The method comprises: (1) designing and blueprinting functionally equivalent immunologic engineered tissues that form the basis for the human immune system (vaccination site (VS), lymphoid tissue equivalent (LTE)); (2) providing communication pathways between the engineered tissue and immunological constructs; and (3) integrating the engineered tissues and immunological constructs in a modular immunobioreactor to form the basis for an in vitro AIS that can be used, for example, in rapid vaccine assessment.

Approaches to construction of the artificial immune system include the construction of engineered immunological tissues, populated with a reproducible cell source, with a particular focus on dendritic cells (DCs). The ability to optimize the spatial juxtaposition and temporal relationships between the cells, biomolecules, and scaffolds via a directed self assembly process moves far beyond existing two-dimensional (2D) Petri dish cell cultures into reproducible three-dimensional, (3D) heterogeneous, biologically viable constructs, much more similar to the in vivo situation.

The present invention further relates to the method of using the AIS, including for (1) assessing the ability to modulate the immune system in a subject to eliminate various of infectious diseases and pathogens; (2) rapid comparison of vaccine or immunotherapy formulations; (3) rational dissection of vaccine or immunotherapy action to identify rate limiting steps to focus further development; and (4) systematic determination of optimal formulations to create better vaccines that promote more rapid and long lived protection. The predictive value of such an engineered tissue construct equivalent immune system is superior to current in vitro models of human immunity.

BRIEF DESCRIPTION OF THE FIGURES

FIGS. 23(A) and 24(B) illustrate well-based embodiments of the present invention, suitable for automation.

FIGS. 26(A) and 27(B) illustrate integration of scaffolds in a 96-well format.

DETAILED DESCRIPTION OF THE INVENTION

Figure 1A:
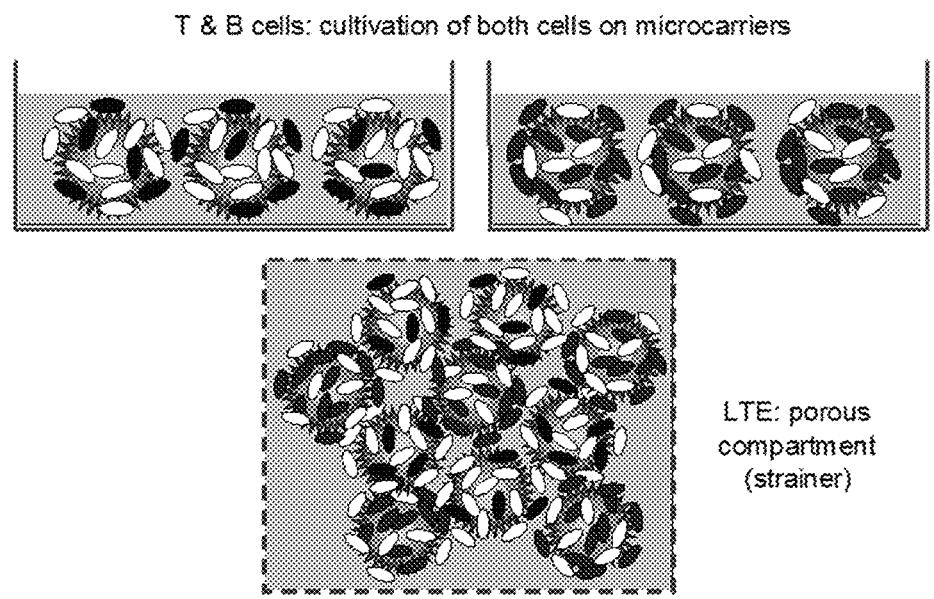
FIG. 1(A) is a schematic representation of an LTE in which T and B cells are cultivated together on microcarriers and then transferred to a porous container

A primary objective of the present invention is to provide an integrated human tissue, specifically an integrated human immune system, for testing vaccines, immunotherapies, adjuvants, drugs, biologics, cosmetics, and other chemicals in vitro. One aspect of the invention relates to methods to construct an integrated human immune system model that comprise using appropriate in vitro cellular and tissue constructs or their equivalents to mimic the normal tissues that interact with vaccines in humans. Such an integrated platform of human tissues enables acceleration of vaccine development strategies and testing of drugs that interact with the immune system. Furthermore, it enables a reduction in animal testing and enables candidate vaccines to be re-engineered and retested at a fraction of the cost of animal studies and human trials.

Tissue engineering involves the development of synthetic or natural materials or devices that are capable of specific interactions with cells and tissues. The constructs combine these materials with living cells to yield functional tissue equivalents. Tissue engineering involves a number of different disciplines, such as biomaterial engineering, drug delivery, recombinant DNA techniques, biodegradable polymers, bioreactors, stem cell isolation, cell encapsulation and immobilization, and the production of 2D and 3D scaffolds for cells. Porous biodegradable biomaterial scaffolds are required for the 3D growth of cells to form the tissue engineering constructs. There are several techniques to obtain porosity for the scaffolds, including fiber bonding, solvent casting/particulate leaching, gas foaming/particulate leaching, and liquid-liquid phase separation. These produce large, interconnected pores to facilitate cell seeding and migration. As used herein, the terms "tissue-engineered construct" or "engineered tissue construct" ("ETC") include any combination of naturally derived or synthetically grown tissue or cells, along with a natural or synthetic scaffold that provides structural integrity to the construct.

It is known that 3D biology is important to induce proper functionality of immunological ETCs (see, e.g., Edelman & Keefer, *Exp. Neurol.* 192:1-6 (2005). A principal approach to studying cellular processes is to culture cells in vitro. Historically, this has involved plating cells on plastic or glass supports. Cells grown on solid or filter support are referred as two-dimensional (2D) cultures. Such 2D cultures on porous supports have been extremely useful for studying many aspects of biology. However, much more in vivo-like conditions can now be realized in 3D cultures. For example, many epithelial cells, both primary cultures and established lines, form complex epithelial structures when grown in 3D ECM.

Recently, in model in vitro lymph nodes, it has been shown that 3D interstitial tissue matrix facilitates not only T cell migration toward an APC, but also supports motility upon cell-cell interaction. A 3D collagen matrix environment, because of its spatial architecture, provides traction for lymphocyte crawling, mimicking some structural features of the lymph node cortex. This provides experimental justification for the importance of a 3D environment in the constructs that comprise the in vitro immune system.

Differences between 2D and 3D microenvironments include that:

(1) in 2D cultures, cells experience unnatural, anisotropic, external cues from the artificial support, while in 3D cultures, cells are able to migrate on the ECM in all dimensions;

(2) in 2D cultures, the support (e.g., plastic, glass) is far more rigid than naturally occurring ECM;

(3) cells grown in 3D culture are more resistant to apoptosis, and (4) proteins secreted by cells can better interact with and be organized by a 3D culture surrounding ECM and influence cell behavior.

The design of the in vitro artificial immune system (AIS) of the present invention comprises:
1. basic, functional, immunological tissues:
   a. skin and/or mucosal equivalent (the vaccination site),
   b. a lymphoid tissue equivalent (LTE (the lymph node), and
   c. blood vascular network equivalents to connect the other two tissues,
2. a cell source for reproducible and repeatable testing, and
3. a bioreactor to house and integrate the immunological tissues and rapidly assess and test vaccine efficacy.

The AIS of the present invention further comprises:
(a) an in vitro skin and/or mucosal-equivalent scaffold (vaccination site, VS) that facilitates trafficking of blood monocytes and non-monocytic dendritic cell (DC) precursors and supports their natural conversion into mature antigen presenting dendritic cells within the artificial skin 3D tissue-engineered construct;

(b) a vessel-like pathway from the vaccination site to the lymphoid tissue equivalent (LTE) for mature DC migration and a blood vessel-like pathway for monocyte migration into the vaccination site (VS);

(c) a lymphoid tissue equivalent in a tissue-engineered scaffold with a structure that mimics lymph node geometry and contains appropriate lymph node cell types;

(d) the above constructs that are functionally equivalent tissue constructs that exhibit comparable properties to endogenous tissues;

(e) integration of these immunological tissue constructs in a bioreactor system.

4. the design and construction of a lymph node-like structure (the LTE) in a 3D scaffold with a structure that mimics lymph node geometry and contains appropriate lymph node cell types, cytokines and chemokines;

5. facilitation of an approach to create tunable microenvironments to study initiation of the immune response via a model of the lymph node's T zone in the LTE design and the use of both synthetic and natural extracellular matrix (ECM) materials, to achieve 3D structures that provide a physical structure mimicking the lymph node's "open" reticular network, containing lymphocytes and biochemical cues (such adhesion motifs and chemokine gradients) expected by lymphocytes in secondary lymphoid tissues;

6. in the LTE, providing the lymph node-like function of T cell help for B cell antibody production (for example, distinct T and B cell areas within the LTE) can be designed by the combined action of digital printing (directing assembly of T and B cells within distinct zones) and by controlled release technology (using, for example, microspheres releasing T and B cell attractants to maintain T and B cell areas, respectively);

7. to assist in self organization of the LTE, BLC (B lymphocyte chemoattractant, MV10 kDa), MIP-3β (macrophage inflammatory protein-3β, CCL19), and SLC (secondary lymphoid tissue chemokine) chemokine microspheres for controlled release within the LTE matrix; additionally, microspheres may be co-printed with T and B cells into LTE scaffolds (in an alternative embodiment, microspheres can be directly encapsulated within the "struts" (e.g., using polycaprolactone) of the hydrogel matrix during polymerization in a criss-cross pattern, much like a "Lincoln log") (in still another embodiment, FRC-engrafted T cell areas can be used, assuming the stromal cells guide T cell localization within scaffolds);

8. use of an engineered, cellular microfluidic, environmental bioreactor that can sustain multiple immunological ETCs and be used to mimic the human immune system;

9. in some embodiments, use of a miniature 3D housing with internal channels through which a nutrient-rich liquid is pumped to "feed" the immunological cells. The walls of these channels can be modified to allow endothelial cell attachment, creating an artificial endothelium, or are fabricated from a biologically compatible material that does not alter cell behavior. Nutrient fluid primes the system before various cells are injected (via syringe initially); in some embodiments, the complete AIS can then be functionally connected to a pumping that simulates blood flow for the nutrient/oxygen solution. In an embodiment, a pulsed pumping mechanism is used to better mimic the situation in vivo. Embodiments of miniature size and transparent architecture enable examination of the components in situ under a microscope.

In another embodiment of the LTE, adjacent T and B cell zones are created, thereby mimicking the natural separation of B and T zones in a lymph node in vivo. In this embodiment, T and B zones of the LTE can be created using microcarriers. Much is now known about the cultivation of cells on microcarriers; these are particles typically about 100 to about 5000 microns in diameter, rough-surfaced or porous, often coated with components of the extracellular matrix (ECM), on which a variety of anchoring-dependent cells can grow and proliferate. The model system is akin to particles in a box. Suitable matrix materials for the microcarriers include lymphoid tissue particulate ECM material, protasan, collagen, protasan/collagen mixes, PLGA (poly(lactide-co-glycolide)), and mixtures thereof.

Figure 1B:
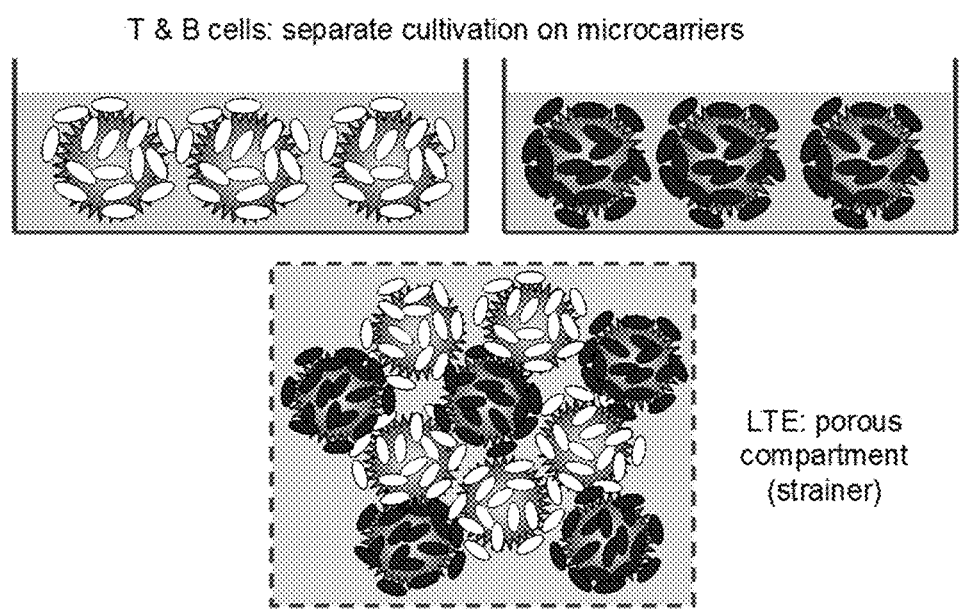
FIG. 1(B) is a schematic representation of an LTE in which T and B cell are cultivated on separate microcarriers and then brought together in a porous container.
Figure 1C:
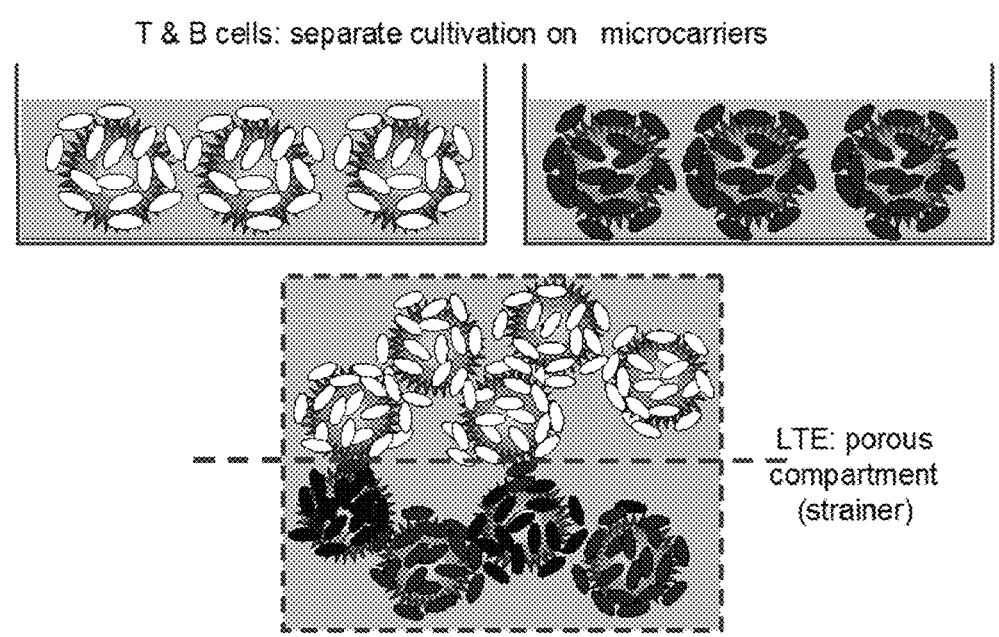
FIG. 1(C) is a schematic representation of an LTE in which separate T and B cell microcarriers are cultivated on separate microcarriers and then brought together in a porous container with separate compartments.

A general approach to creating such a LTE comprises:

1. loading microcarriers with appropriate adhesion ligands, such as chemokines, for the attachment of T and B cells; the microcarriers can be natural or synthetic, dense or porous and of various sizes depending on the desired packing density;

2. culturing T and B cells on the microcarriers; the T and B cells can be cultivated together (FIG. 1A), or cultivated separately on their respective microcarriers (FIGS. 1B, 1C);

3. bringing together the T and B cell-populated microcarriers in contact in a porous container (akin to a "tennis ball basket"); and 4. allowing the microcarriers to pack 'intelligently;' such packing density allows cell penetration.

There are sequential steps in the generation of an immune response to a vaccine in a mammal. First, a vaccine acts on immune cells in the skin, gut, or mucosal site of vaccination to activate cells. Second, after immunization with a vaccine, dendritic cells (DCs) migrate out of the site to the draining lymph node via lymphatic highways. Third, dendritic cells in the draining lymph node (or other secondary lymphoid tissues) interact with T and B cells to activate antigen specific lymphocytes that are capable of activating further immune responses, eliminating the pathogen through multiple effector mechanisms and transforming into memory cells with long term memory of antigen.

This three-step process is mimicked functionally in the AIS of the present invention. First, the antigen/pathogen acts on immune cells in the in vitro vaccination site (VS, e.g., skin equivalent or mucosal tissue equivalent) to activate antigen presenting cells and start the maturation process. Second, as cytokines, chemokines, and chemicals are produced at the site of vaccination, dendritic cells migrate out of the site to the lymphoid tissue equivalent (LTE) via endothelial vessels and complete their maturation process. Third, dendritic cells in the LTE interact with T and B cells to activate antigen-specific lymphocytes that are capable of activating further immune responses, eliminating the pathogen through multiple effector mechanisms and transforming into memory cells with long-term memory of antigen.

The AIS comprises immunological tissue constructs corresponding to the basic steps in vaccine or immunotherapy action. To functionally reproduce these steps, the AIS comprises tissue engineered constructs:

an in vitro VS scaffold that facilitates trafficking of blood monocytes and non-monocytic dendritic cell precursors and supports their natural conversion into mature antigen-presenting dendritic cells within the artificial VS construct, paths from the vaccination site (VS) to the lymphoid tissue equivalent (LTE) for dendritic cell (DC) migration, and a lymphoid tissue equivalent (LTE) in a scaffold with a structure that mimics lymph node functionality and contains appropriate lymph node cell types.

These functionally equivalent tissue constructs exhibit comparable properties to endogenous tissues. These functionally equivalent tissue constructs are integrated in a modular bioreactor. The AIS is designed to perform high-throughput vaccine and immunomodulator screening in an ex vivo immune system that provides the appropriate repertoire of T and B cells within a bioreactor system.

The In Vitro Lymphoid Tissue Equivalent (LTE)

The ultimate output of a vaccine occurs in the lymphoid tissues, where antigen-specific T and B cells are activated and partly convert to memory cells that have been notoriously difficult to detect in vitro. To mimic a natural immune response in vitro, the present invention comprises a lymphoid tissue equivalent (LTE), essentially an artificial lymph node, that can be connected with the vaccination site (VS). In vivo, vaccine-derived antigen is transported to lymph nodes by diffusion along lymphatic vessels to lymph node cells, or by migration of mature DCs that have internalized the antigen, to the draining lymph node. In the lymph nodes, DCs activate antigen-specific T cells and, in conjunction with helper T cells, help to activate antigen-specific B cells to elicit an immune response.

The strength and quality of the T and B cell responses depend on the amount of antigen delivered and on the subtype and maturation state of the DC (APC) carrying the vaccine-derived antigen. Two- and three-way interactions between the key cells (dendritic cells, B and T cells) occur in spatially segregated regions of the lymph nodes in a sequential order of events. To simulate this process, an artificial lymphoid tissue or lymphoid tissue equivalent can be constructed with lymph node-like features and spatial organization in vitro using a combination of tissue engineering, materials science, and biological studies. For example, immune cells are highly responsive to chemokine gradients, and thus the design of scaffolds containing organized gradients of these signaling molecules allows the synthetic lymph node tissue to self-organize, in a fashion similar to that in native tissue. The formation of native tissue can also be studied in parallel to uncover further molecules to help form in vitro-organized tissues. Such complex synthetic structures can also be fabricated, e.g., using the digital printing BioAssembly Tool (BAT).

In an embodiment of the present invention, once the LTE is assembled, it is also possible to use it as a "biofactory," biosynthesizing various desired biomolecules (such as cytokines, proteins, antibodies). For example, if an antigen is presented to B cells, they can create antibodies in the LTE. Potentially, the created antibodies could also be monoclonal, depending on the repertoire of B cells and how the peptide is presented to the B cells.

The artificial immune system can have a general bioreactor design that is mechanistically different than the natural immune system, though similar in terms of functionality.

In an embodiment, the immunological ETCs are integrated in a miniature, engineered, cellular environmental bioreactor. This design uses two functionally equivalent membranes in a sequential order to create a functional VS and localized collections of T and B cells on or around particles, to function as the LTE.

Important design considerations are to emulate biological functions, minimize media volume between zones to increase efficiency of cell trafficking, and provide a means of evaluating antigenic responses. By integrating and minimizing the media volume, potential for cell migration within and between the immunological ETCs is dramatically enhanced and can provide an increased immunological response.

However, it is not necessary to have the VS and LTE in an integrated bioreactor. In an alternative embodiment, mature DCs from the VS can be physically positioned in the LTE. These mature DCs can activate T cells within the T cell zones and B cells within the B cell zones of the LTE. Thus, it will be possible to test and characterize both the VS and LTE and the interactions between the mature DCs from the VS and the T cells in the LTE in a non-integrated fashion.

The general, basic cascade of events for AIS operation is as follows:

monocytes and other blood-derived cells (PBMCs) are injected into the blood vascular highway;

chemokines (either natural to the VS or intentionally added) attract monocytes to enter into the VS;

monocytes differentiate into immature DCs (iDCs);

iDCs mature in response to "vaccination" (comprising introduction of antigen) in the VS;

chemokines attract mature DCs;

chemokines (either natural to the LTE or intentionally added) attract mature DCs into the LTE; and mature DCs in the LTE activate T and B cells.

Monocytes and dendritic cells will naturally interact and migrate across the vascular endothelia. In other embodiments chemokines can be used to direct the migration of the cells, as can magnetic microbeads. Magnetic beads together with miniaturized electromagnets are a convenient mechanism for manipulation of cells in a bioreactor. For example, cells with appropriate surface markers (receptors, epitopes) can be selected using the beads and selected cells can be transported from one local environment to another, bringing cells in contact with, e.g., desired surfaces, environments, or other cells (see Examples).

The Bioreactor

In embodiments of the present invention using an integrated AIS bioreactor, a nutrient-rich liquid is pumped through internal channels in a 3D housing to 'feed' the immunological cells. The walls of these channels can be modified to allow endothelial cell attachment, creating an endothelium, or are fabricated from a biologically compatible material that does not alter cell behavior.

In an embodiment, laser micromachining with ultra-short pulse lasers is used to design and fabricate the channels so that the fluid flows well. In other embodiments, microstamping, laminates, or standard CNC, and other milling processes can be used.

Cells within such constructs will be exposed to culture medium (nutrients).

The complete artificial immune system can then be connected to a pump that simulates blood flow for the nutrient/oxygen solution. In an embodiment, the pumping mechanism can also be pulsed, to better mimic the blood vasculature. The entire assembly can then be inserted into an incubator that regulates temperature, humidity, and concentrations of oxygen and carbon dioxide to best simulate the natural in vivo environment.

In an embodiment, the bioreactor system can be constructed to be of the order of a few inches in total size, potentially allowing the in vitro immune system bioreactor apparatus to be built into other stationary and portable analytical instruments. Embodiments of miniature size and optical transparency allow viewing of the components in situ using a microscope.

There are physical and practical limitations on LTE construct design and size. Physical volumes for the constructs are based on estimates of the desired cell populations for secondary and primary immunological responses, respectively. The numbers also assume, as an example, a particular packing density of the cells within the constructs (e.g., 68%).

Figure 2A:
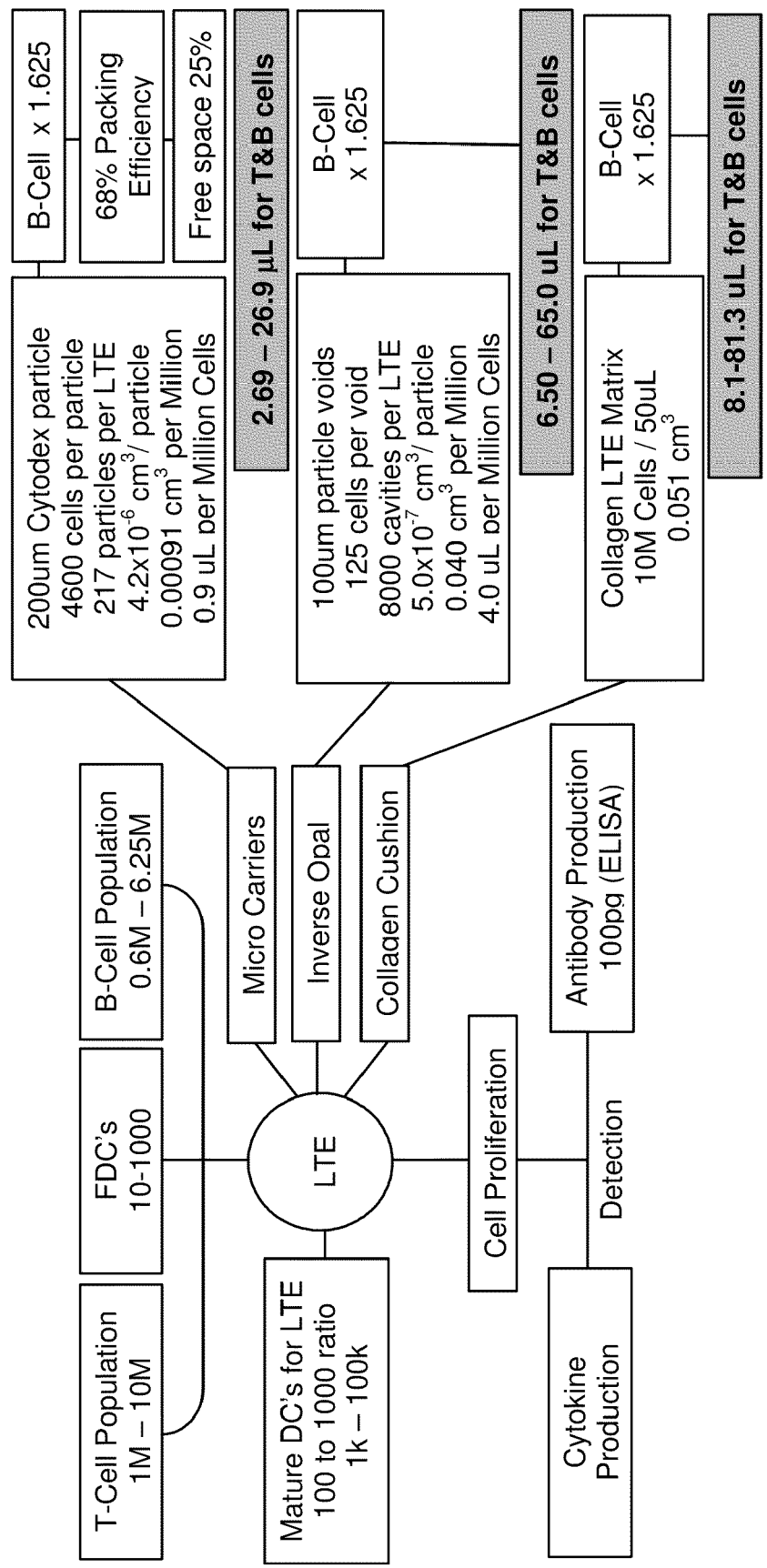
FIGS. 2(A) and 2(B). Practical considerations in AIS design.
Figure 2B:
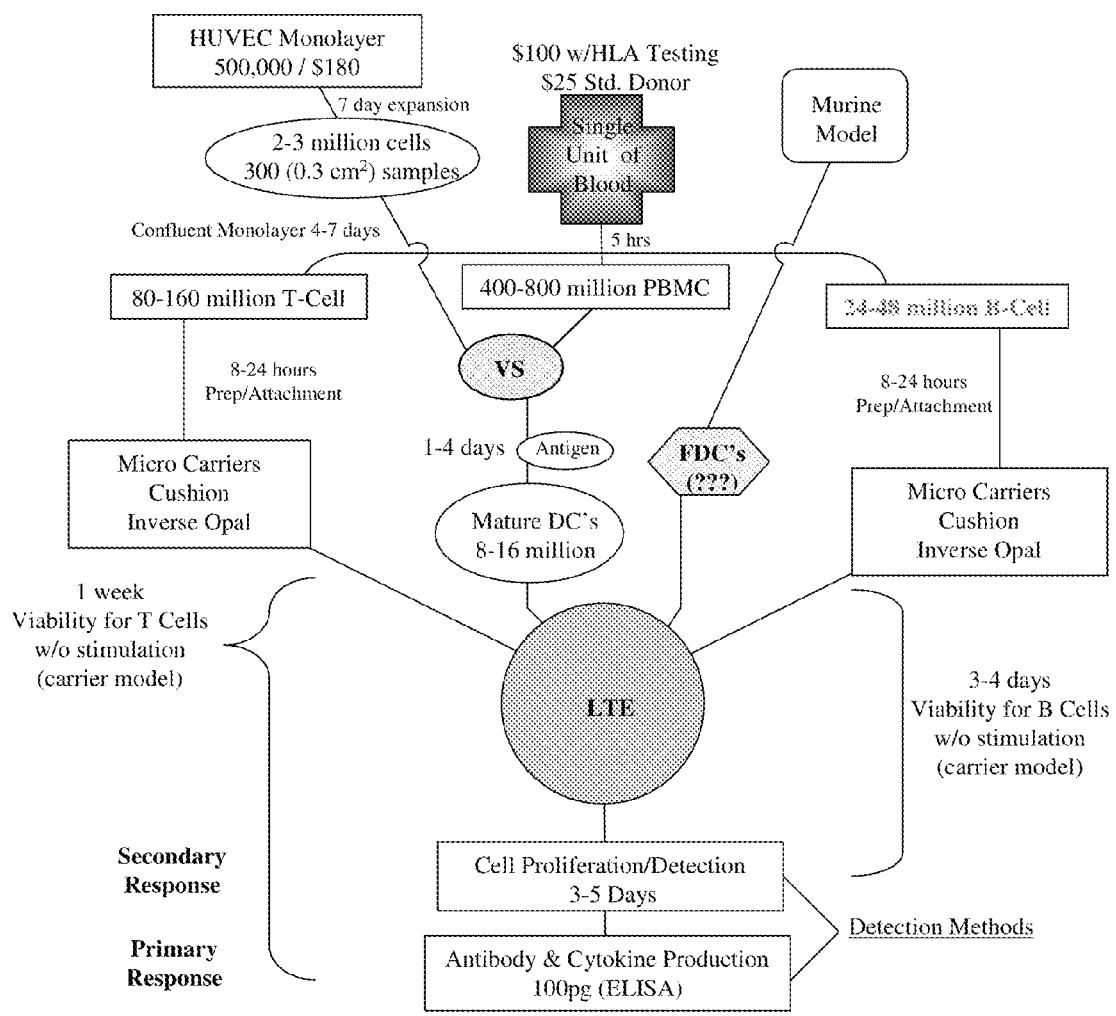

For Reference:
Scale Volume
$1 \times 1 \times 1$ mm=0.001 $cm^3$ or 1 μL
10 million cells (~6 μm cell diameter)=0.0021 $cm^3$ or 2 μL
Diameter×Height=Cylinder Volume 2.3 mm×1 mm=0.004 cm$^3$ or 4 µL 5.7 mm×3 mm=0.077 cm$^3$ or 84 µL 6.6 mm×3 mm=0.103 cm$^3$ or 103 µL FIGS. 2a and 2b illustrate other practical considerations for AIS design and function, such as cell culturing times and how many T and B cells can be obtained from a unit of blood to populate the AIS (this example uses PBMCs as the cell source). In an embodiment of the invention, the T to B cell population ratio is approximately 1.6 T cells per B cell, mimicking that seen in a lymph node. In an embodiment of the invention, to examine a primary immunological response, the system comprises approximately 10 million T cells and 6.3 million B cells.

Other embodiment of the AIS of the present invention facilitate automation and high-throughput testing. Embodiments of the present invention include the static AIS model and an integrated model described below. In other embodiments, collagen and other ECM membranes can be housed in a well-based bioreactor. Various features in the examples presented include:

- simplicity (e.g., can be incorporated into a 96-well format).
- inexpensive.
- compatibility with several LTE models.
- compatibility with, e.g., membrane and cushion VS models.
- VS and LTE preparation sequences can be kept separate and the constructs can be integrated later.
- low dead volumes.
- compatibility with single and reverse DC transendothelial migration schemes, using various VS models.
- incorporation of micro-dialysis filtration to reduce or replace media exchange and keep important cytokines in the microenvironment.

Although many of the examples pertaining to embodiments that use multi-well based systems use a 96-well microarray plate, any multi-well format can be used. For example, Thermo-Fast® 24 and 28 well plates can be used; 8 and 12 thermo-strips by Abgene can be used; Nunc® 16-well slides can be used; as well as standard 384 well and 1536 well microarray plates. Microarray plates include plates that are intended for tissue or cell culture, i.e. tissue culture plates. The methods of the invention are not intended to be limited by either the size of the multi-well format, or the manufacturer of the multi-well format.

Using the AIS, it is possible to rapidly test and evaluate the immune response to vaccines and other substances. Several concepts are presented to organize the tissue and activate it appropriately to receive vaccines, antigens, or other chemicals of interest. In one embodiment, the integrated engineered tissue constructs incorporate chemotaxis and engineered-release microparticles to allow control of temporal, spatial, and dose parameters of various biomolecules for tissue and cell assemblage and programming. In another embodiment, constructs provide an environment that enables the stroma and parenchyma to self-assemble into a native-like tissue via communication achieved through cell-cell, cell-matrix, structural and endogenous growth factor cues that the cells themselves create; no exogenous growth factors may be necessary to induce given phenotypes.

The practice of the present invention will employ, unless otherwise indicated, conventional methods of immunology, histology, microbiology, cell and tissue culture, and molecular biology within the ordinary skill of the art. Such techniques are explained fully in the literature. All publications, patents, and patent applications cited herein are incorporated by reference in their entirety.

EXAMPLES

Example 1

Designer Scaffold Structures

Figure 3:
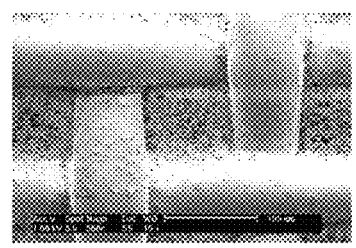
FIG. 3 shows HUVEC cells growing on protasan/collagen matrix on a nylon mesh. High-magnification SEM of the nylon membrane and interspersed Protasan/collagen matrix material is shown in the top image. Seeding of the primary layer of HUVEC cells was accomplished on an inverted membrane (left, Side 1), then 24 hours later, brought to an upright position (right, Side 2) where the second layer was applied. Phase contrast images of each plane of HUVEC cells is shown in the center two lower images, with the left being the first layer, and the right being the second layer applied.
Figure 3:
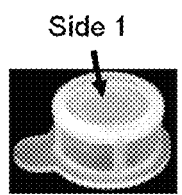
Figure 3:
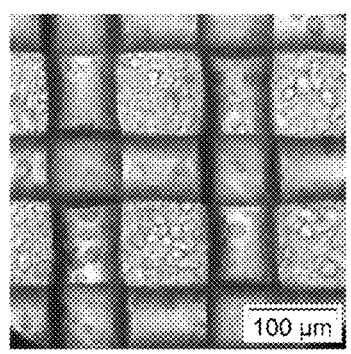
Figure 3:
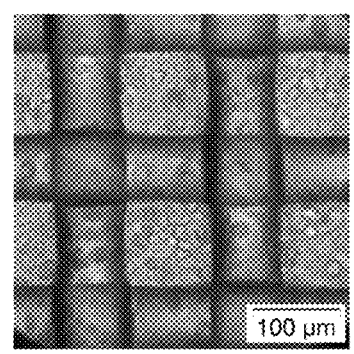
Figure 3:

Designer scaffold structures were constructed to test cell viability, cell motility, and nutrient flow for bioreactors and have studied cell motility as a function of construct stability for collagen gels. FIG. 3 shows HUVEC cells growing on protasan/collagen matrix on a nylon mesh. High magnification SEM of the nylon membrane and interspersed Protasan/collagen matrix material is shown in the top image. Seeding of the primary layer of HUVEC cells was accomplished on an inverted membrane (left, Side 1), then 24 hours later, brought to an upright position (right, Side 2) where the second layer was applied. Phase contrast images of each plane of HUVEC cells is shown in the center two lower images, with the left being the first layer, and the right being the second layer applied.

Example 2

Digital Printing Technology

Figure 4:
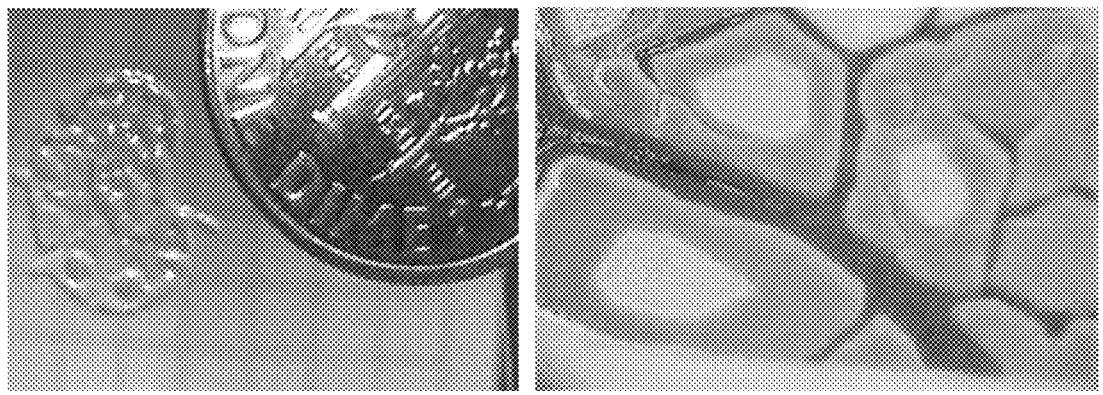
FIG. 4 shows mockup of digitally printed lymph node (left panel) and a retinal image of vasculature (right panel).

Preliminary hardware and software ETC heterogeneity digital printing prototypes have been developed. FIG. 4 shows the mockup of a digitally printed lymph node and a retinal image of vasculature. This mockup lymph node comprises six biocompatible hydrogel layers, four different patterns, and three materials. The vasculature image has been built with multiple layers of biodegradable construction material with feature sizes that range from about 100 to about 3,000 microns. The objects were fabricated with three dispensing nozzles each.

Example 3

LTE Structure

The LTE serves as an important locus for activation of naive T and B cells. The present invention includes, in the design of the LTE, multiple approaches for fabrication of a model of the lymph node extracellular matrix and providing various microenvironemental cues (such as chemokines, cytokines, cells (e.g., fibroblastic reticular cells)). Specific design considerations for the LTE include T cell activation and DC survival/function within the LTE and fabrication of LTE structures comprising both T and B zones. These can be assembled using several complementary strategies.

a. Direct physical assembly of segregated T and B cell areas.

b. Self organization and maintenance of T and B cell areas via creation of engineered local chemokine sources within distinct locations within the matrix.

The following description sets out in detail the experimental rationale and approach for each of these features of the present invention.

Example 4

Microbeads Fabricated from Lymphoid Extracellular Matrix

Microbeads were fabricated from porcine lymphoid extracellular matrix prepared using a protocol provided by Dr. Stephen Badylak, University of Pittsburgh.

Figure 5:
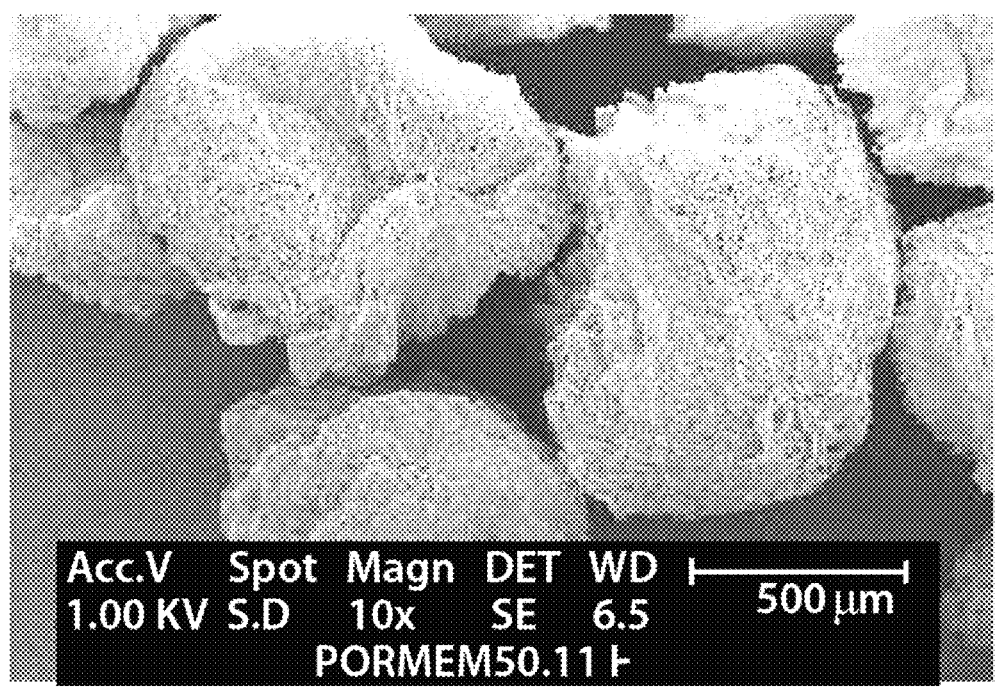
FIG. 5 shows image of microbeads fabricated from lymphoid ECM (80% w/w) and Protasan (20% w/w) by flash freezing, freeze drying, and gelation with tripolyphosphate.

A suspension containing ~10 mg/ml lymph node (LN) ECM microfragments in 2 mg/ml Protasan, pH 3.5, was sprayed over the surface of liquid nitrogen in a laminar, drop-by-drop mode, making droplets of about 1.5 mm in size. The frozen beads were then freeze dried overnight, incubated in 10% tripolyphosphate (TPP), pH 6.0, for 1 hour thereafter, then washed three times with deionized water over a 100 μm cell strainer, and were then freeze-dried again (FIG. 5).

Example 5

In Vitro Tissue Slice Templates

Additional approaches to constructing a functional LTE. The embodiments above describe an approach to fabricating a minimal, functional mimic of mammalian, preferably human, secondary lymphoid tissue. Other embodiments considered within the scope of the present invention are now described.

Figure 6:
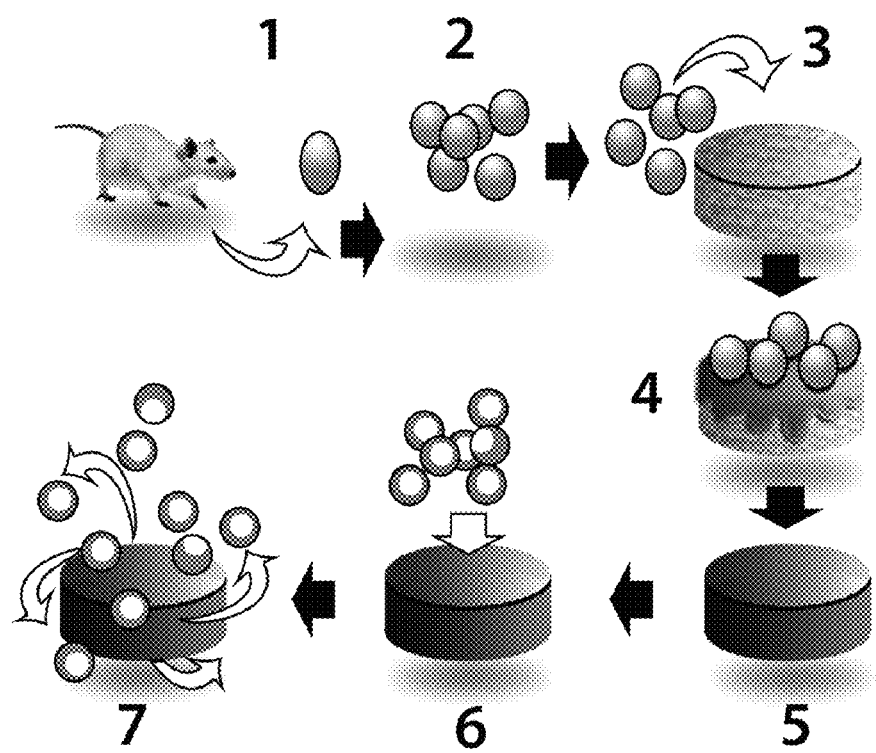
FIG. 6 shows an additional embodiment involving 'templating' the LTE using native human stromal cells in a manner similar to that reported by researchers attempting to create an in vitro artificial thymus (Poznansky, et al., *Nat. Biotechnol.* 18:729-734, (2000)).

Another embodiment involves 'templating' the LTE using native human stromal cells (FIG. 6), in a manner similar to that reported by researchers attempting to develop an in vitro artificial thymus (Poznansky, et al., *Nat. Biotechnol.* 18:729-734 (2000)). Their approach comprised the following steps:

1. small thymus fragments from mice were cultured on the surface of Cell Foam disks (a porous matrix) in 12-well plates and covered in growth media for 14 days until a confluent layer of stroma had formed throughout the matrix.
2. upon reaching confluence, human lymphocyte progenitor cells were added into the co-culture.
3. during co-culture for 4 to 21 days, non-adherent cells were periodically harvested and cell surface markers were analyzed to determine T lymphopoiesis.

Following a similar scheme, in an embodiment of the present invention, LTE matrices could be "templated" with stromal cells derived from lymph node fragments or lymph node, spleen, or tonsil "slices" to seed the construct with native stromal cells and provide a ready microenvironment for added T cells, B cells, and DCs. Such cocultures can be maintained in vitro using standard organ culture methods during the templating step, and the templated LTE can subsequently be loaded into the AIS bioreactor for continued maintenance. This approach not only provides an alternative for generating a correct lymphoid microenvironment, but also a complementary in vitro approach for analysis of lymph node formation and organizing principles.

Example 6

Bioreactor Design and Construction: Integration of the AIS Components

Drawing an analogy with high throughput drug screening technology, an AIS suitable for rapid vaccine or chemical screening can use multiple, low-cost, disposable bioreactors, designed for single-use. Each bioreactor will be challenged with a different antigen and, upon activation of the immune response, harvested for antibodies, B cells, and T cells.

In an embodiment of the present invention, microfluidic bioreactors can be used to achieve this goal. They provide the additional advantage of requiring low numbers of scarce cells for seeding tissue constructs.

Figure 7:
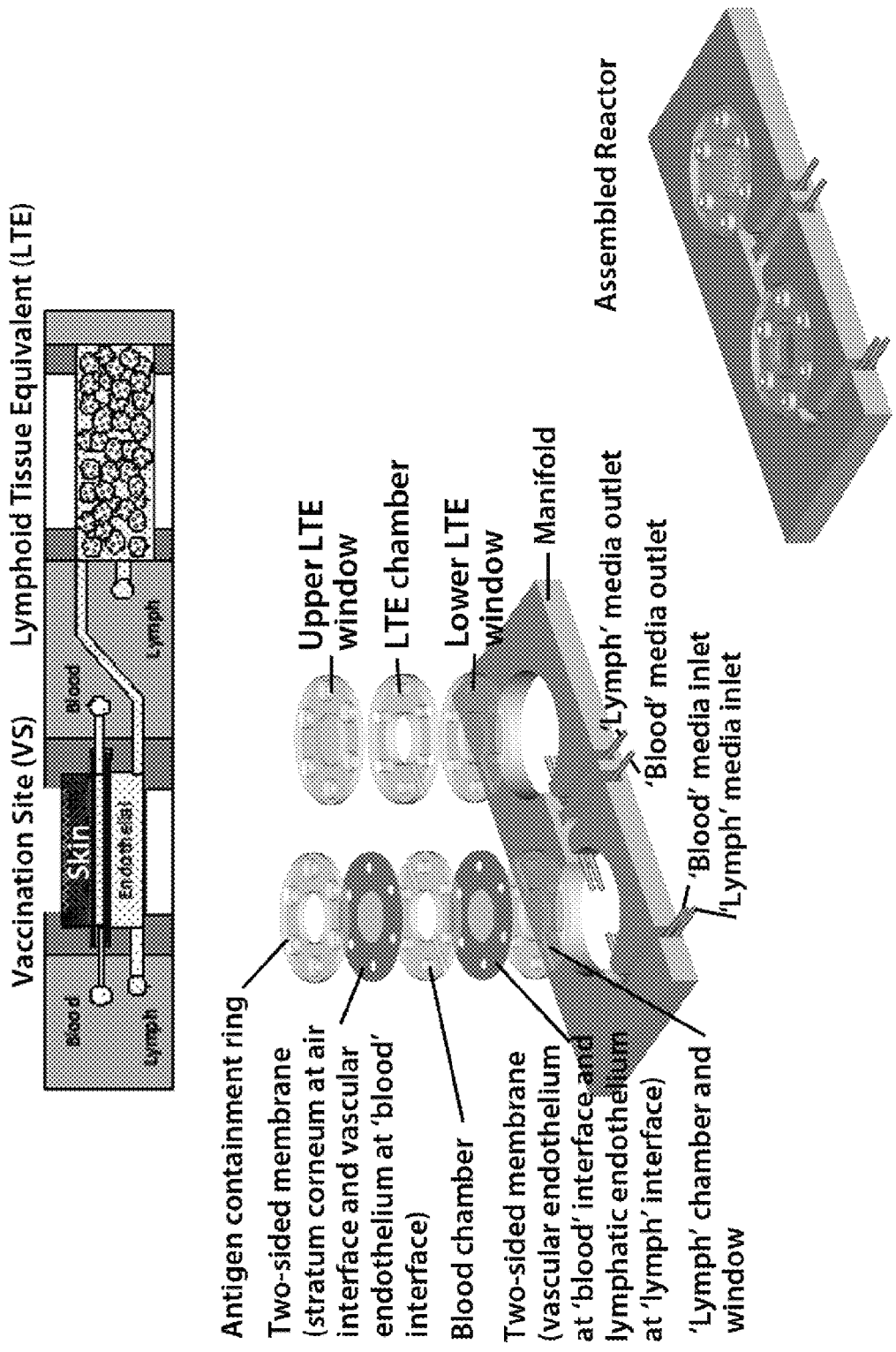
FIG. 7 shows a schematic of a bioreactor.
Figure 8:
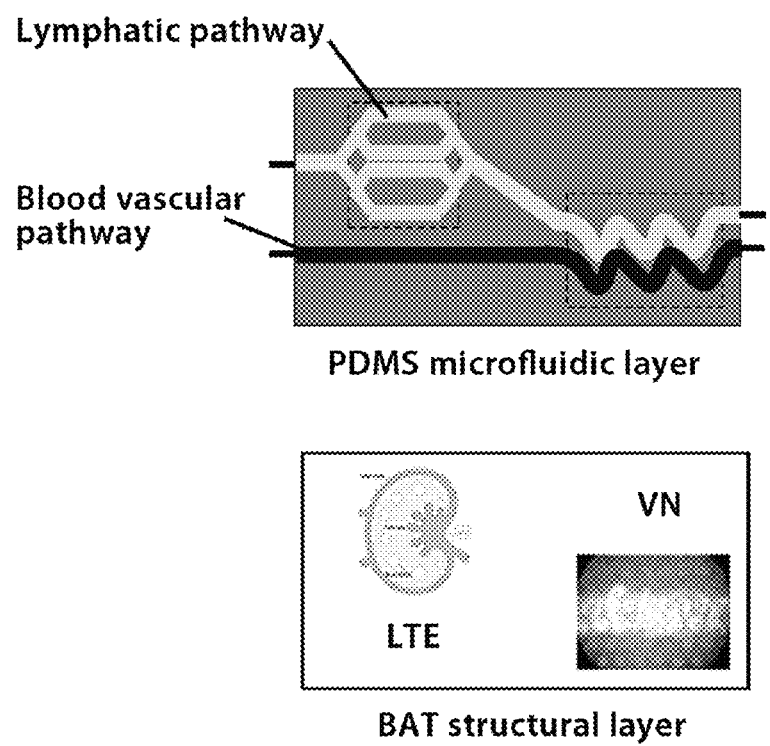
FIG. 8 is a plan view of an example integrated bioreactor that shows micromachined endothelial pathways with high contact area (left panel) beneath the VS and LTE ETCs (right panel).

As illustrated in FIG. 7, in an embodiment of the present invention, the AIS bioreactor can be fabricated as a two-compartment microscope slide with a transparent polymer sheet or glass coverslip for microscopic examination. In a preferred embodiment, the physical dimensions of each immune bioreactor measure on the order of about 7.5 cm long and about 2.5 cm wide, with an overall thickness of about 2 mm or less. The first chamber contains the VS and LTE membranes that can be grown as modular units and later inserted into the lower structural layer or as a fully integrated system from the start. The second chamber contains the LTE, comprising T and B cell populations. If required, additional LTE constructs can be added to enable lymphoid organ trafficking or trafficking to other tissues. Syringe tube ports located on the upper layer permit injection of factors and/or cells at strategic positions along the vascular pathways and within ETCs. FIG. 8 shows a plan view of an example integrated bioreactor that shows micromachined pathways with high contact area beneath the VS and LTE ETCs.

Figure 9:
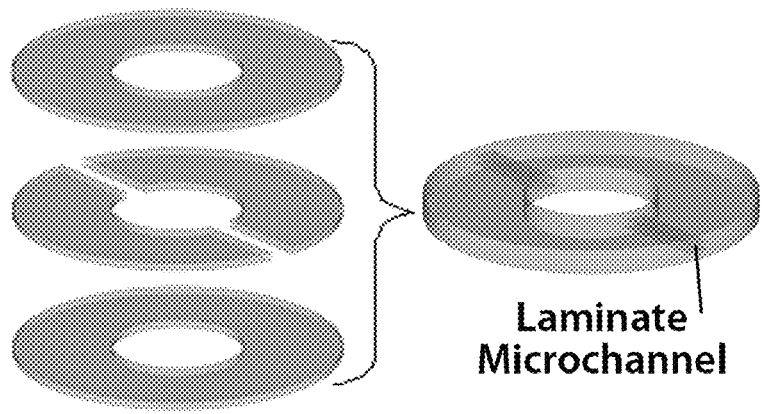
FIG. 9 shows a laminate based insert whereas a larger milled tubular design is incorporated in to the design illustrated in FIG. 13.

To promote interaction between cells migrating along pathways and in the VS and LTE tissue constructs, the contact spacing between each tissue membrane can be adjusted by using, e.g., machined inserts or thin laminates that have small, integrated microchannels. Suitable construction materials include biologically compatible polymers, such as polycarbonate, polyethylene, and acrylic. A laminate-based insert is as shown in the example (FIG. 9), where as a larger milled tubular design is incorporated in to the design illustrated in FIG. 7. In a sense, these designs mimic a thin venule pathway that supports lymphocyte migration from peripheral blood into secondary lymphoid organs.

Nutrient-rich media can be pumped from an external media reservoir through the channels, flowing tangentially past the VS and LTE constructs, and back to the reservoir. Nutrient and waste product transport between the recirculating media and the tissue constructs occurs through both diffusional and convective (Starling flow) processes.

Figure 10:
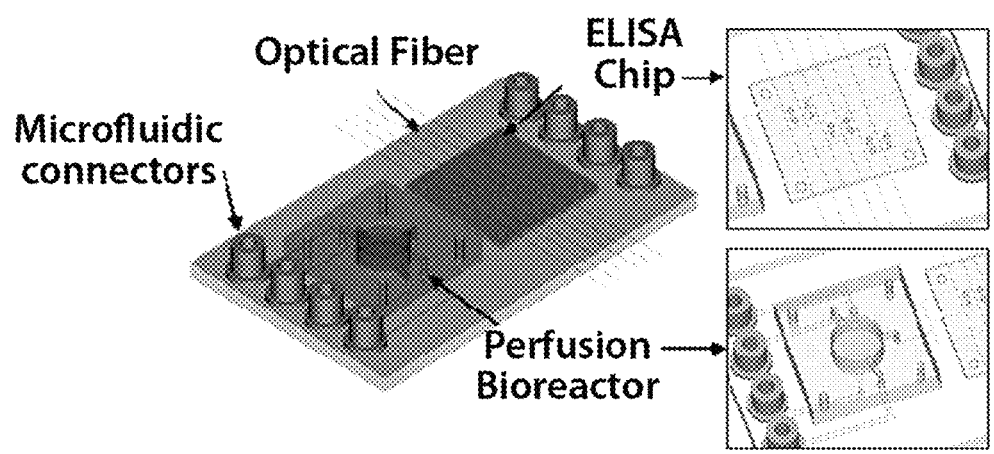
FIG. 10 shows an example microfluidic bioreactor with optical diagnostics on microfluidic backplane.

In contrast to other nutrients, oxygen is only sparingly soluble in cell culture media. Consequently, high perfusion rates may be required to sustain a sufficient oxygen supply and to avoid developing necrotic zones. Should required perfusion rates exceed physical capabilities (e.g., unusually high pressure drops can compromise the integrity of bioreactor seals) or generate excessive fluid shear, in alternative embodiments, the oxygen tension in the media may be increased by, for example, using an $O_2$ microexchanger in-line with the circulating blood media. By circulating the blood media over gas permeable polymers, exposed to high oxygen concentrations on the opposite side, the $O_2$ environment can be adjusted to compensate for any $O_2$ consumption and loss. Monitoring and making adjustments to the $O_2$ concentration in the bioreactor can be accomplished using commercially available non contact fluorescent probes to provide feedback to an oxygen air supply. Creating a high concentration gradient between the gaseous oxygen at the polymer interface and the tissue construct, can facilitate diffusional transport and culturing of thicker constructs. An example of an assembled construct with transparent covers for optical inspection/fluorescent imaging is shown in FIG. 10.

Example 7

Fabrication and Assembly of Layered AIS

Fabrication of such microfluidic bioreactors may require ultra short pulse machining trials with the biocompatible materials to determine optimum processing conditions (such as laser fluence and translation speed). The design of the present invention is sufficiently flexible to allow laser machining of a layered device (e.g., gas permeable polymer top layer, BAT deposited middle layer, and PDMS bottom layer) for additions of vias or ports after the device has been assembled.

Figure 11:
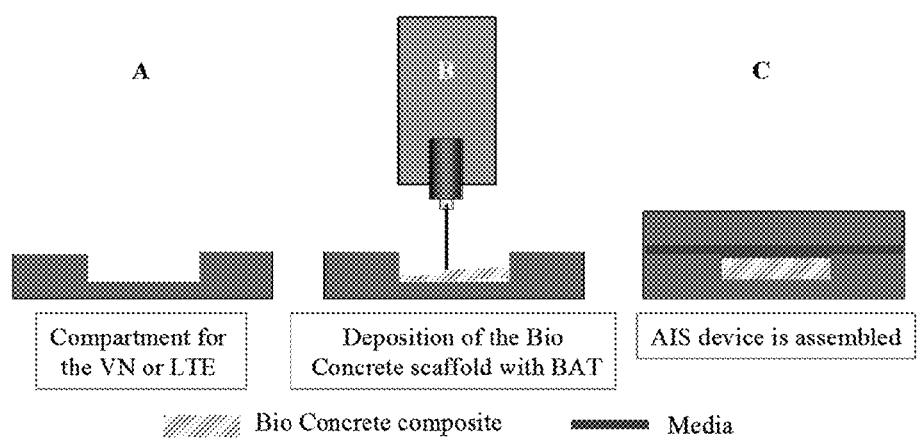
FIG. 11 shows cross sectional views of direct deposition in the AIS device. Various biomaterial structures can be incorporated as constituents of the artificial immune system (e.g., bio concrete, colloidal particles, ECM gels, collagen gels, microcarriers). For example, a polymeric mesh rebar can be deposited layer by layer directly in the recessions of the VS and LTE areas. In such a design, it is preferred to have the lower plate of the AIS unit made of polyacrylate, polystyrene, or another transparent plastic sensitive to DM, to allow the mesh rebar to attach to the plate. In this embodiment, the surface is micro-patterned using KOH in a manner similar to the ESC scaffolds. Fibrin gel matrix bearing all necessary nutrients and cytokines can be used to coat the threads of the mesh as a thin film, leaving sufficient space for cell accommodation and motion.

FIG. 11 shows cross sectional views of direct deposition in an embodiment of an AIS device. Various biomaterial structures can be incorporated as constituents of the artificial immune system (e.g., bio concrete, inverse hydrogel opal, colloidal particles, ECM gels, collagen gels, microcarriers). For example, a polymeric mesh rebar can be deposited layer by layer directly in the recessions of the VS and LTE areas. In such a design, it is preferred to have the lower plate of the AIS unit made of polyacrylate, polystyrene, or another transparent plastic sensitive to DM, to allow the mesh rebar to attach to the plate. In this embodiment, the surface will be micropatterned using KOH in a manner similar to the ESC scaffolds. Fibrin gel matrix bearing all necessary nutrients and cytokines will be used to coat the threads of the mesh as a thin film, leaving sufficient space for cell accommodation and motion.

Figure 12:
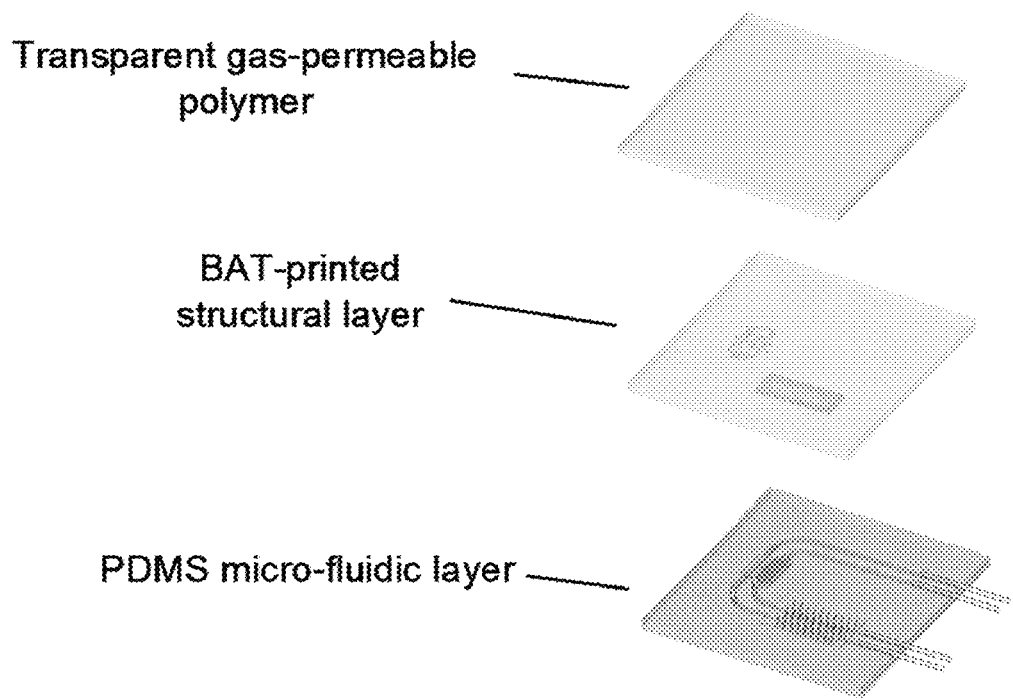
FIG. 12 shows an example microfluidic bioreactor in separate layers.
Figure 13:
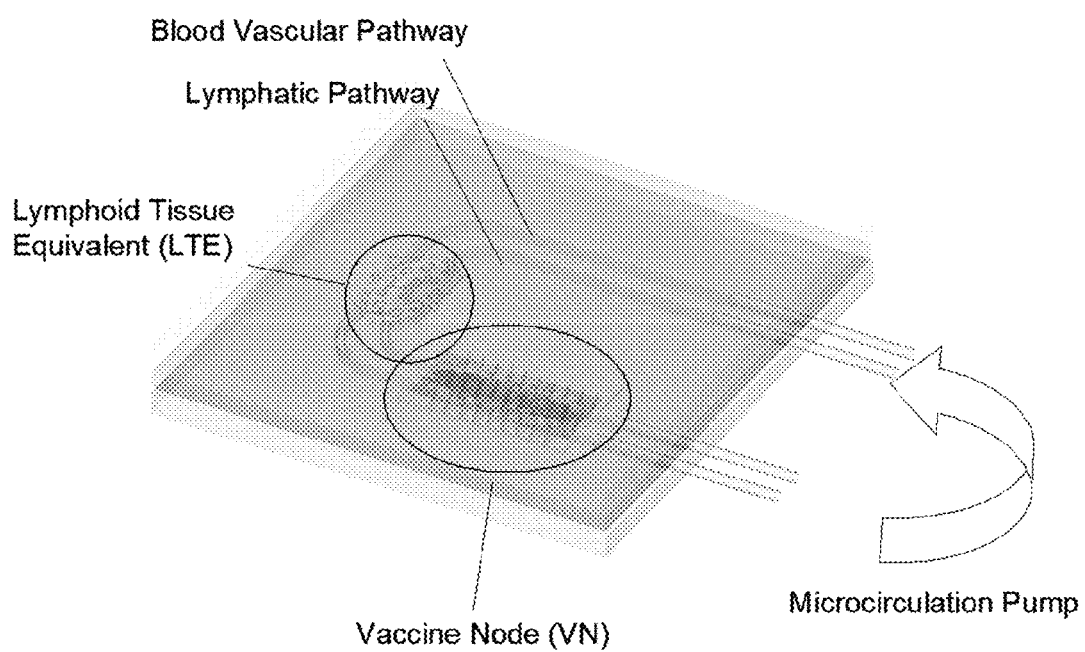
FIG. 13 shows an assembled microfluidic bioreactor.
Figure 14:
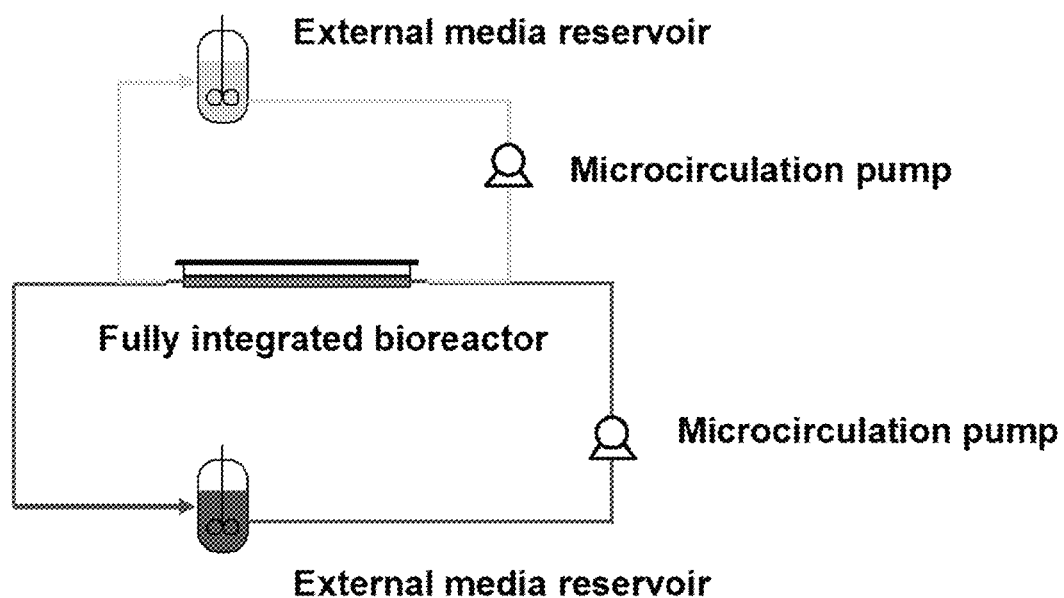
FIG. 14 is a schematic diagram of a perfused bioreactor system with the associated external pumps for vascular loops and external media reservoirs. The AIS bioreactor can be operated in semi-batch or continuous mode.

As shown in FIGS. 12 and 13, the design of the present invention is sufficiently flexible to allow laser machining of a layered device (e.g., gas-permeable polymer top layer, BAT-deposited middle layer, and PDMS bottom layer). FIG. 14 provides a schematic diagram of a perfused bioreactor system with the associated external pumps for the lymphatic and blood vascular loops and external media reservoirs. The AIS bioreactor can be operated in either semi-batch or continuous mode.

Figure 15:
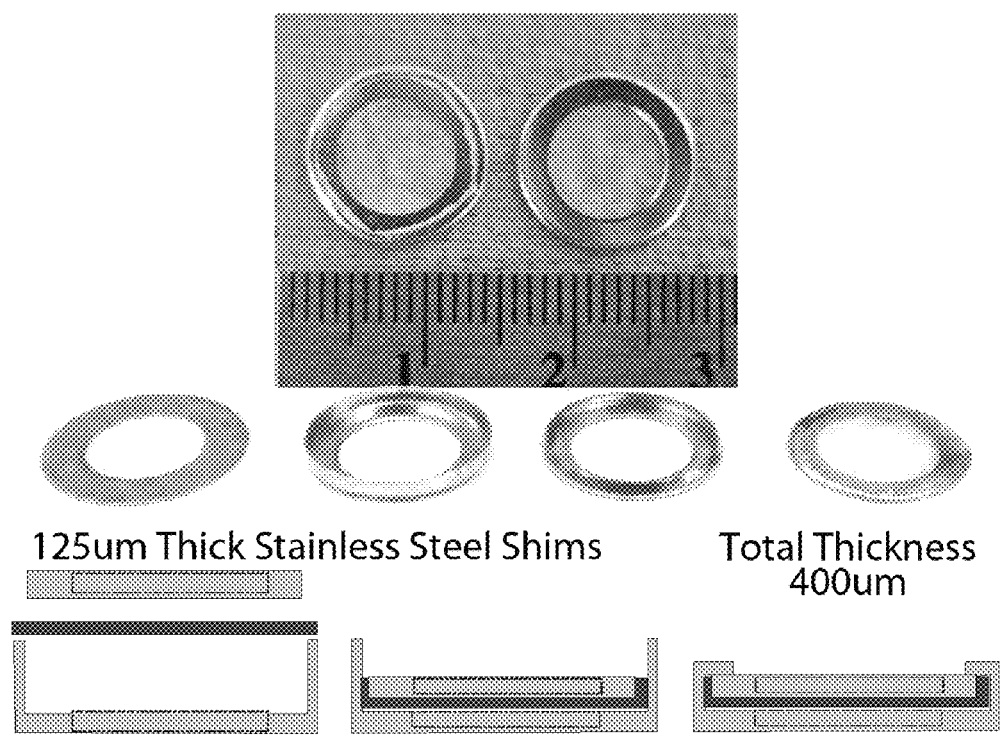
FIG. 15 shows membranes between thin metal (e.g., stainless steel) rings. Using such a crimping method, biological membranes can be supported without use of adhesives and can be pressed into a disk with thickness profile of about 400 μm or less.

In an embodiment of the present invention, integration of membranes in the bioreactor is achieved by crimping the membranes between thin metal (e.g., stainless steel) rings, as illustrated in FIG. 15. Using such a crimping method, biological membranes can be supported without use of adhesives and can be pressed into a disk with thickness profile of about 400 μm or less.

Figure 16:
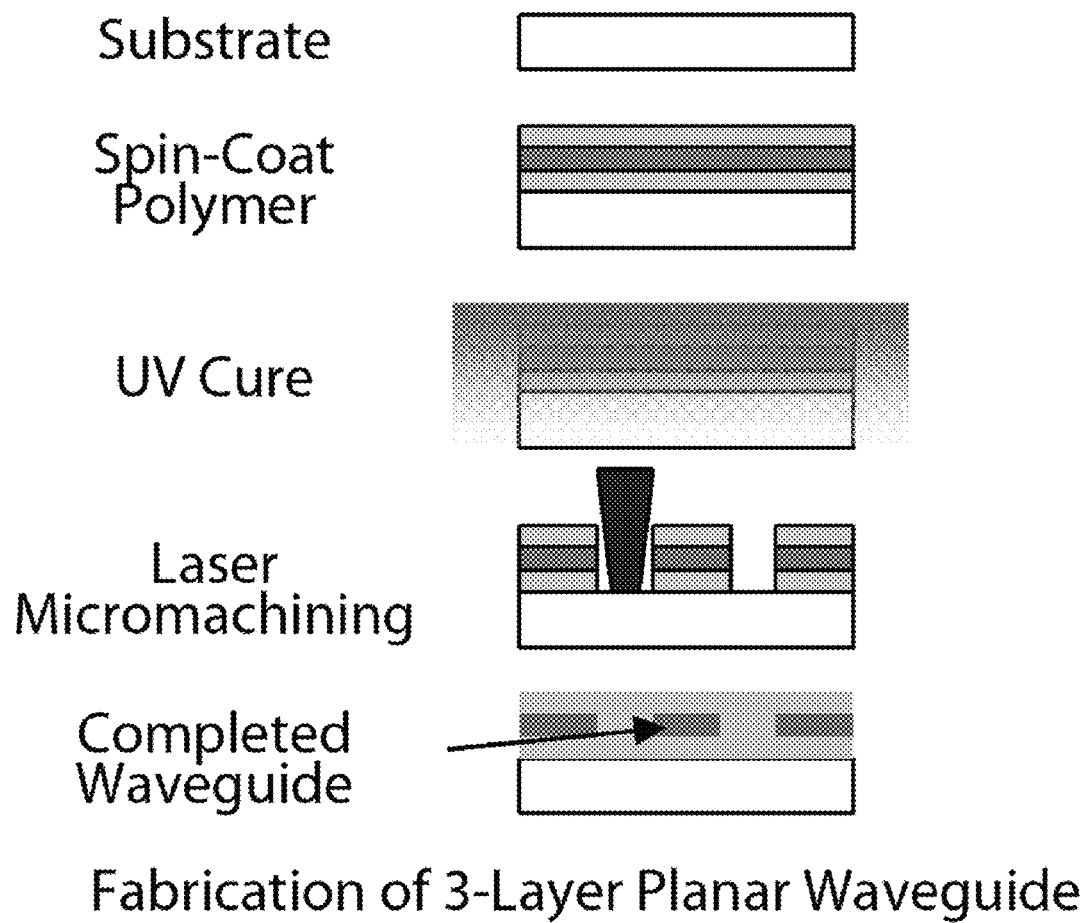
FIG. 16 is a schematic showing the fabrication of a 3-layer planar waveguide.
Figure 17:
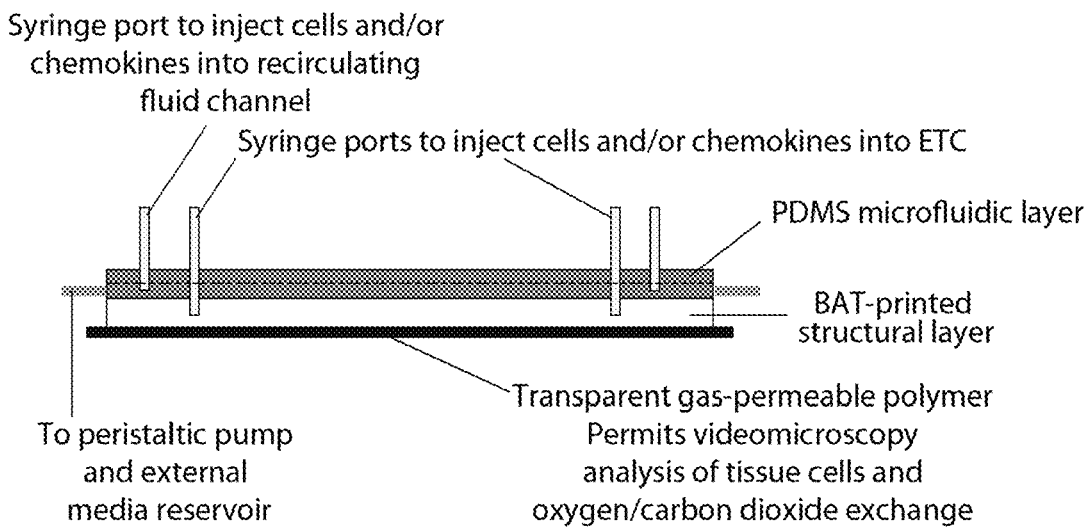
FIG. 17 shows an example device comprising a perfusion bioreactor, an ELISA chip with integrated optical waveguides, microfluidic backplane to connect and allow swapping of devices and microfluidic connectors for external pumps and reservoirs.

FIG. 16 shows the fabrication of a 3-layer planar waveguide. FIG. 17 shows an example device comprising a perfusion bioreactor, ELISA chip with integrated optical waveguides, microfluidic backplane to connect and allow swapping of devices and microfluidic connectors for external pumps and reservoirs.

In addition to machining channels directly, molds can be machined in suitable materials to create a reusable master from which PDMS devices may be formed. This will allow a higher volume of devices to be fabricated than laser machining in serial. Channel encapsulation methods will be evaluated to provide a leak-proof construct. The materials that comprise the device will likely be damaged at high temperatures, so robust, low-temperature bonding methods will be needed.

Testing of the devices will require fixtures for mounting and providing external connections. Laser machining can also be used to provide manifolds for these test fixtures that would support fast swapping of devices without the need to disconnect external pumps or reservoirs. Equipment for measuring pressure, flow resistance and flow rate can also be connected to the devices via the manifold. Revisions to optimize the channel geometries can be made based on this data and performance of the ETCs.

An AIS microfluidic bioreactor system can be placed in an incubator that maintains constant temperature, humidity, and carbon dioxide control. Phenol red can serve as a colorimetric pH indicator in the media, so that pH can be monitored, e.g., periodically through visual inspection or photometric determination with logging capabilities. In another embodiment, pH can be monitored continuously and precisely in the external media reservoir with a pH probe and recorder.

Figure 18:
FIG. 18 is a picture of synthetic and natural membranes supported by stainless steel rings.

Creating insert supports for both synthetic and natural membranes has been accomplished by using laminates, crimped rings, and adhesives (FIG. 18). Laminates and adhesives have primarily been used to support polymer meshes, which in turn provide mechanical strength to synthetically formulated biological membranes. Fabrication using the laminate comprises sandwiching a stretched mesh between two pieces of polymer laminates, which are then thermally sealed together. The adhesive method comprises stretching a mesh support and adhering a stainless steel ring using a biocompatible glue. The crimping method, discussed earlier, comprises compressing the membrane between two stainless steel rings. Generally, the laminate and adhesive methods are limited to synthetic mesh-supported membranes, while the crimping method can accommodate both natural biological membranes and synthetic meshes.

Example 8

Optically Diagnostic AIS Microfluidic Bioreactor

Immunology has many cascades of events that cannot be observed in any human system at this time. In particular, if a vaccine fails as a result of a rate-limiting step related to entry into and interactions within an immunological tissue, there is presently no method to measure or improve this process in humans. To address this problem, an embodiment of the present invention include building the AIS in such a way as to be able to optically monitor in situ the steps of the in vitro immunological/vaccination process.

In one embodiment, integrated optical waveguides become part of a micro-total analytical system (μTAS) of the AIS, with many different functions including optical excitation, absorption, fluorescence, and imaging on a single microfluidic bioreactor system. An in situ diagnostic system will make optimization and conducting diagnostic evaluations of the immunological constructs more rapid. Two-photon fluorescence can enable visualization of immunological events in all three dimensions in both artificial and living tissues. This technique can aid in understanding and optimizing the effects of various adjuvants, vaccine candidates, drugs, biologics, biomolecules, and antigen presentation vehicles in vitro and with in situ diagnostics.

Prototype results are presented regarding fabrication of μTAS that can be used to perform the immunological analysis steps in situ, to simplify the process and reduce analysis time. In one embodiment, the present invention provides an AIS device with the addition of integrated optical waveguides for in situ optical diagnostics. These waveguides provide optical excitation and detection pathways for colorimetric analyses (such as ELISA assays, absorption and fluorescence analysis).

In this example, single layer, planar polymer waveguides were fabricated using selective femtosecond laser ablation of a polymer substrate. A glass slide was coated with an 80 μm-thick layer of a single part, ultraviolet curing polymer with a refractive index of 1.56. After curing for 30 minutes with a ultraviolet (UV) lamp (4 W), planar optical waveguides and microfluidic channels were machined into the polymer using a Ti:sapphire femtosecond regime laser. The optical waveguides and microfluidic channels were each approximately 100 μm wide by 80 μm deep. Light from a CW Nd:YVO$_4$ laser was coupled to the planar waveguides through a 50 μm core diameter optical fiber inserted into a tapered alignment groove as shown on the left. Light guided through the planar waveguides passes through an intersecting microfluidic channel. This waveguide/channel intersection is shown in the middle with the laser source off and on the right with the laser source on. Light entering the channel from the right is collected in the waveguide on the opposite side of the channel. This light is then coupled to another 50 μm core optical fiber and sent to a silicon detector for measurement.

Example 9

In Situ Diagnostic Bioreactor Development

Microfluidic devices that mimic in vivo systems are proving valuable in studying cell interactions and biological processes in vitro. Such devices offer several advantages over traditional large-scale fluidic assemblies including small sample and reagent volumes, small waste volumes, increased surface area-to-volume ratios, low Reynold's numbers (laminar flow), fast sedimentation for particle separation, reduced reaction times, and portability. Some microfluidic devices also integrate pumps, valves, filters, mixers, electrodes, and detectors. The ease of alignment and shorter reaction times make near real-time detection possible using this approach.

Figure 19:
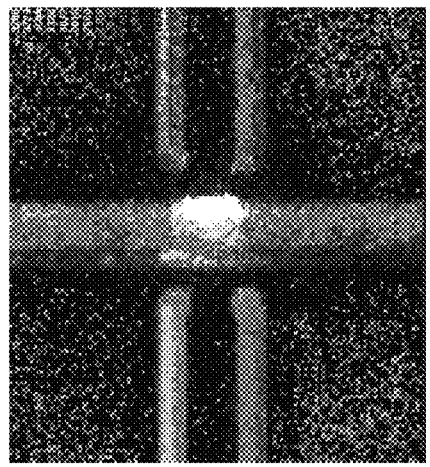
FIG. 19 shows images of an ultra-short pulse laser micromachined planar optical waveguides integrated into microfluidic channel. Left panel: Tapered port for fiber optic coupling. Middle panel: microfluidic channel intersection of planar waveguide (source off). Right panel: microfluidic channel intersection of planar waveguide (source on, entering from right).
Figure 19:
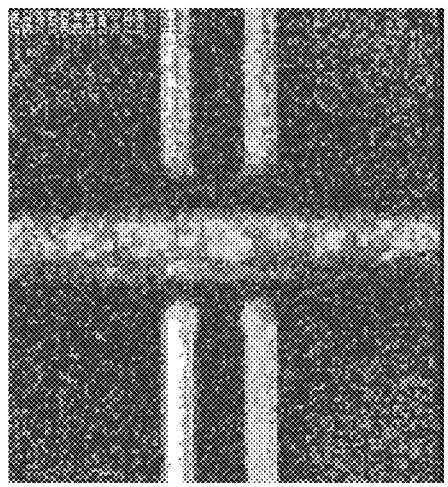
Figure 19:
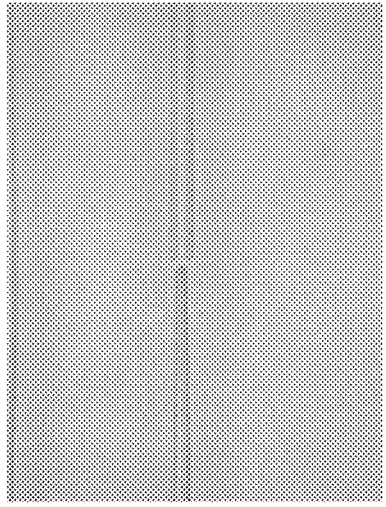

Fabrication of microfluidic devices has relied mainly on technology developed in the microelectronics industry, such as photolithography and subsequent etching of silicon or glass. These technologies often require multiple processing steps and clean room facilities and can take days or weeks to produce a working device; they are better suited to mass production of devices than rapid prototyping. A relatively new method of fabrication is ultra-short pulse laser micromachining (USPLM). USPLM has the advantage that materials can be machined directly without the need for masks or photoresist development. Devices can therefore be fabricated more quickly, often in a day or less, permitting rapid prototyping. Furthermore, due to the extremely short pulse duration (<150 fs) and high intensities, almost any material can be readily ablated because of multiphoton absorption and ionization, even if it is transparent at the laser wavelength. This is especially useful in machining materials for an optically transparent bioreactor. FIG. 19 shows an ultra-short pulse laser micromachined planar optical waveguides integrated into microfluidic channel. Left panel: Tapered port for fiber optic coupling. Middle panel: microfluidic channel intersection of planar waveguide (source off). Right panel: microfluidic channel intersection of planar waveguide (source on, entering from right).

Figure 20:
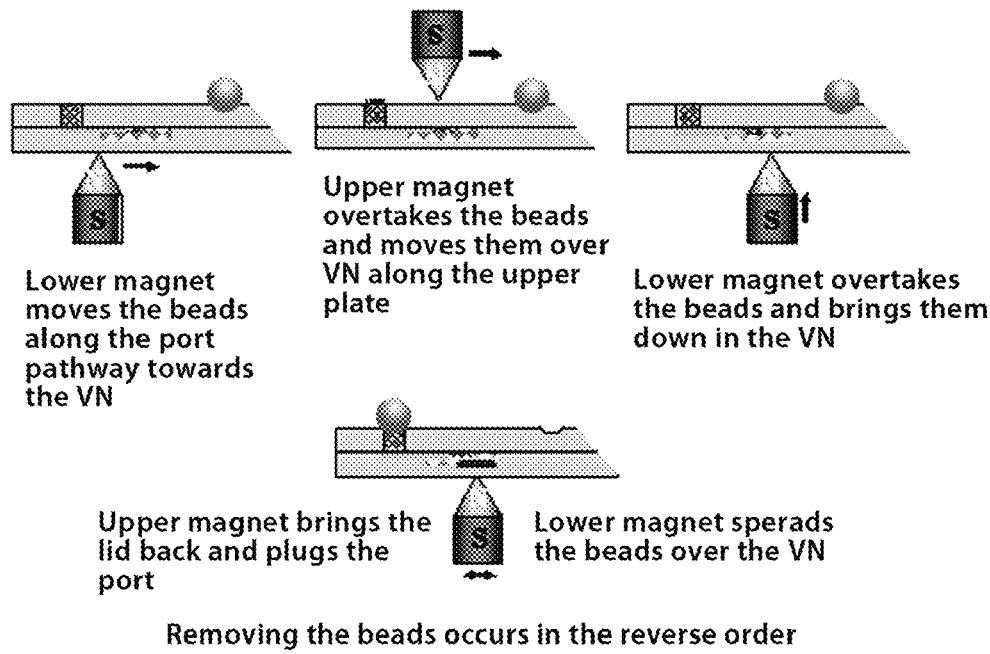
FIG. 20 shows an embodiment of the MaAIS.
Figure 21:
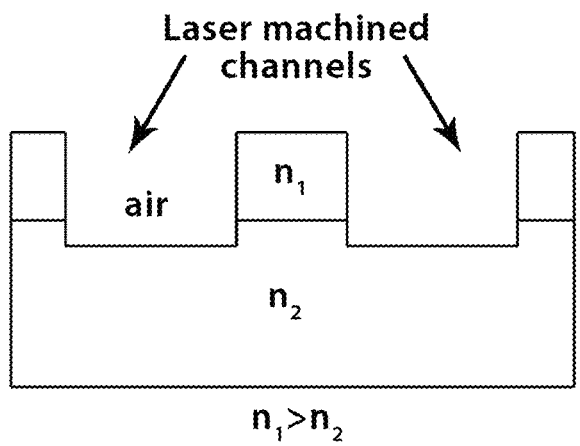
FIG. 21 shows laser machined integrated optical waveguides: n1 represents the refractive index of the waveguide core, $n_2$ is the cladding index.

In an embodiment of the present invention, USPLM was used to machine microfluidic channels, vias, reservoirs, and integrated optical waveguides in the bioreactors. An inexpensive and widely used biocompatible silicone elastomer, polydimethylsiloxane (PDMS), comprises the main body of the structure. Sheets of PDMS can be patterned by USPLM and then assembled to form the 3D construct (*Laser-machined microfluidic bioreactors with printed scaffolds and integrated optical waveguides*, Nguyen, et al., *Proc. SPIE Int. Soc. Opt. Eng.*, 5591). The layers may be either permanently bonded by treating with oxygen plasma or temporarily bonded by applying mechanical pressure. Thus, fabrication of disposable or re-usable devices is easily accomplished In one embodiment, integrated optical waveguides are fabricated as illustrated in FIG. 20. The waveguides comprise multiple alternating refractive index polymer layers in which the middle polymer layer has the higher refractive index. In preferred embodiments, the polymers can be either UV or thermal cured or a combination of both (e.g., PDMS cladding and UV curing core). The waveguides are defined by removing material on either side using an ultra-short pulse laser. The laser can also be used to integrate tapers for fiber optic coupling to the waveguides. Microfluidic channels are machined either parallel or perpendicular to the waveguides. Light is launched into a waveguide on one side of the microfluidic channel, passed through the channel where it interacts with the fluid in the channel and then collected by the waveguide on the opposite side of the channel and sent to a detector. In another embodiment, fiber optics are embedded into PDMS and then microfluidic channels machined perpendicular to the fibers, removing a small section of the fiber in the channel. This eliminates the need for planar polymer waveguides and fiber-to-waveguide coupling losses at the expense of elaborate waveguide geometries, such as splitters and combiners FIG. 21.

Figure 22:
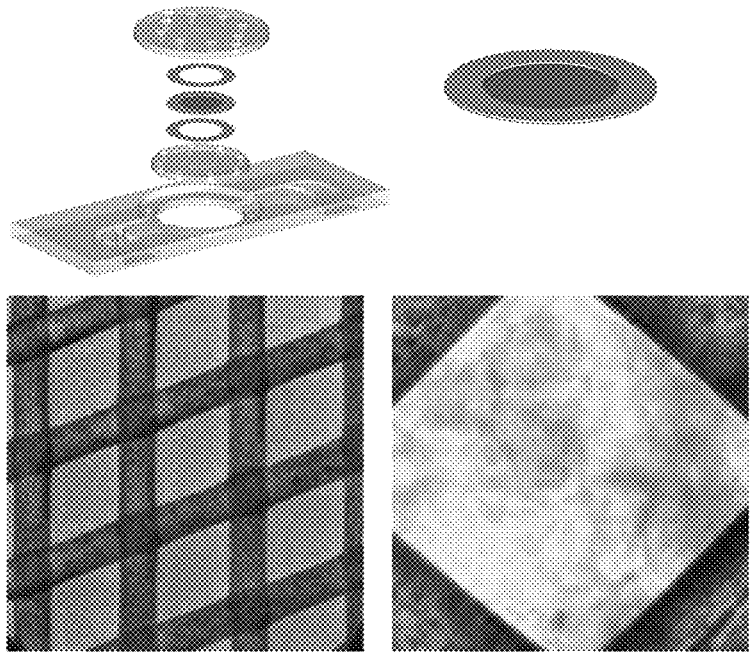
FIG. 22 shows an example bioreactor construction with collagen membranes on rings and support matrix. Panel A shows a bioreactor design. Panel B shows progression from the whole bioreactor to the level of the collagen matrix cushion within the mesh. Panel C shows the assembly of the bioreactor under sterile conditions, after the HUVEC cells have reached confluence on the collagen cushion. Once assembled, media flow can be initiated.
Figure 22:
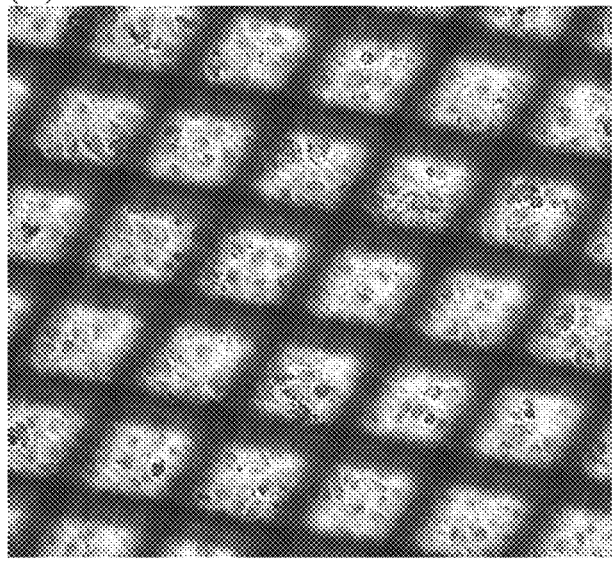
Figure 22:
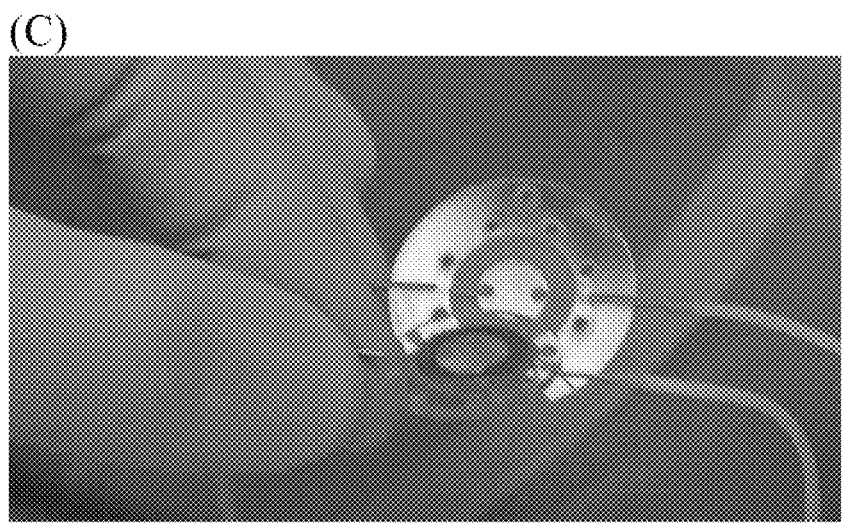

FIG. 22 shows an example bioreactor construction with collagen membranes on rings and support matrix. Collagen cushion congealed at 37° C. for 1 hour remained highly stable with no collagen degradation for more than 3 weeks. Panel A shows the bioreactor design. Panel B shows progression from the whole bioreactor to the level of the collagen matrix cushion within the mesh. After the HUVEC cells have reached confluence on the collagen cushion, the bioreactor is assembled under sterile conditions (Panel C). Once assembled, media flow is initiated.

Example 10

Design of an AIS Device

An example AIS device is illustrated in FIG. 10. The device comprises a microfluidic bioreactor, ELISA chip with integrated optical waveguides, microfluidic backplane to connect and allow swapping of devices and microfluidic connectors for external pumps and reservoirs. The bioreactor has four external ports, two each above and below the tissue construct. An ELISA chip with three sets of two channels is illustrated, though more channels are contemplated in the same footprint in other embodiments. In each set, one channel is for a sample assay and the other is a control with no sample. Each set is attached to the same ELISA input port, allowing both channels to be prepared simultaneously; however, only one channel in a set is attached to the sample fluid. This fluid is pumped from the bioreactor to the ELISA chip through a channel in the microfluidic backplane. Valves control the addition of the sample fluid to each channel. Light is coupled to the ELISA channels through optical fibers and the transmitted light is coupled to another fiber attached to a detector. In this preferred embodiment, the bioreactor and ELISA chips are both optically transparent for two-photon and confocal microscopic examination. In this preferred embodiment, the footprint of the entire assembly in this example is approximately 50×75 mm.

Example 11

Utilizing AIS as a Biofactory

In an embodiment of the present invention, the assembled LTE is used as a "biofactory," biosynthesizing various desired biomolecules (such as cytokines, proteins, antibodies). For example, if an antigen is presented to B cells, they can create antibodies in the LTE. Potentially, the created antibodies could also be monoclonal, depending on the repertoire of B cells and how the peptide is presented to the B cells. Monoclonal antibodies (mAb) are used extensively in basic biomedical research, in diagnosis of disease, and in treatment of illnesses, such as infections and cancer. Antibodies are important tools used by many investigators in their research and have led to many medical advances.

Example 12

Static AIS

Figure 23A:
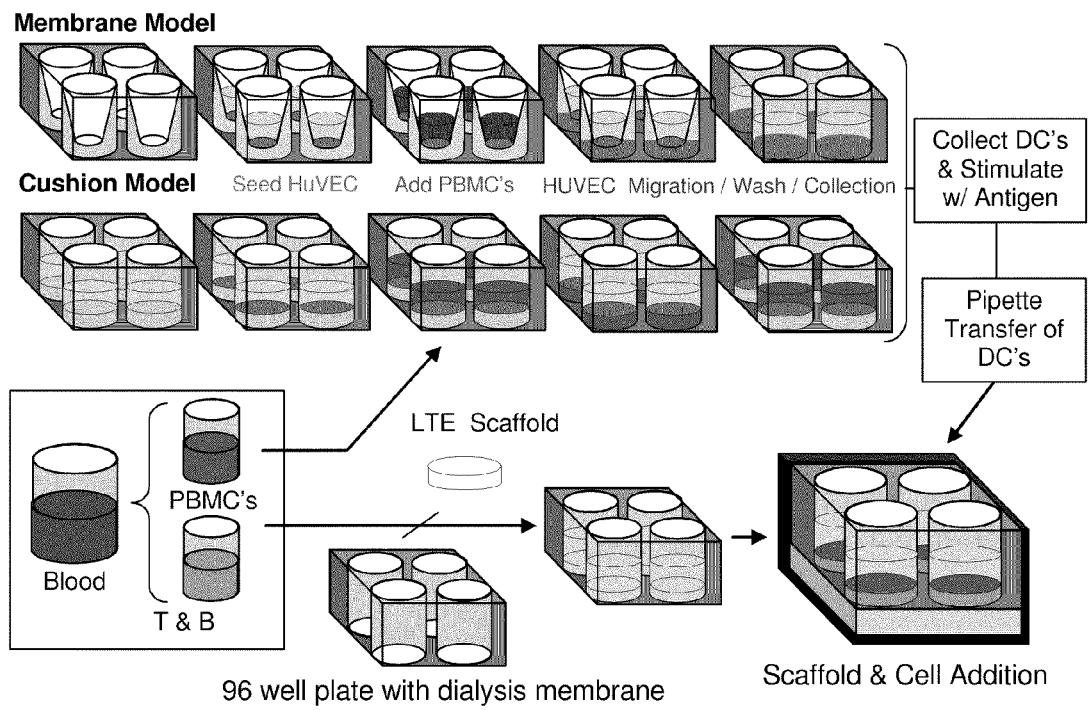

Drawing an analogy with high-throughput drug screening technology, an AIS suitable for rapid vaccine, vaccine formulation, or chemical screening can use multiple, low-cost, disposable bioreactors, designed for single-use. Each bioreactor will be challenged with, for example, a different antigen or antigen/adjuvant combination, and, upon activation of the immune response, harvested for antibodies, B cells, and T cells. An embodiment of the present invention is illustrated in FIG. 23. In this example, a static 96-well plate format is used. The system comprises two parts: the VS and LTE.

The VS comprises a matrix and a plurality of cells attached to the matrix. The cells used in the VS can form an endothelial layer, an endothelium, a vascular endothelial layer, or a vascular endothelium on one or both sides of the matrix. Alternatively, the cells used in the VS can form an endothelial layer on one side of the matrix, and an epithelial layer on the other side; or an endothelial layer on one side of the matrix and an epithelium on the other side; or an endothelium on one side of the matrix and an epithelium on the other side; or a vascular endothelium on one side of the matrix and an epithelial layer on the other side; or an endothelium on one side of the matrix and an epithelial layer on the other side; or a vascular endothelium on one side of the matrix and an epithelium on the other side; or a vascular endothelial layer on one side of the matrix and a lymphatic endothelial layer on the other side; or a vascular endothelial layer on one side of the matrix and a lymphatic endothelium on the other side.

The plurality of cells attached to the matrix in the VS may comprise or be derived from peripheral blood mononuclear cells (PBMCs). Alternatively, the plurality of cells attached to the matrix of the VS may comprise fibroblasts, mast cells, human cells, human vascular endothelial cells (HUVECs), human dermal microvascular endothelial cells (HMVECs), blood vessel endothelial cells, lymphatic endothelial cells, monocytes, dendritic cells, mast cells, macrophages, neutrophils, and fibroblasts. When a vascular endothelial layer or a vascular endothelium is preferred to be formed in the VS, human vascular endothelial cells (HUVECs) or human dermal microvascular endothelial cells (HMVECs) are preferably used.

The matrix used for the VS can comprise a natural biopolymer. The natural biopolymer may be selected from the group consisting of xenographic extracellular matrix (ECM) sheet, reconstituted collagen matrix, and chitosan/collagen membrane scaffolds. In one embodiment, the natural biopolymer is a bovine type I collagen on a nylon mesh or a polycarbonate mesh.

The LTE comprises a matrix and a plurality of lymphocytes and leucocytes attached to the matrix. The plurality of lymphocytes and leucocytes may comprise T cells, B cells, dendritic cells, naïve T cells, naïve B cells, memory T cells, and/or memory B cells. The matrix used for the LTE may comprise synthetic extracellular matrix (ECM) materials, natural ECM material, synthetic lymphoid ECM-derived hydrogel, natural lymphoid ECM-derived scaffolds, or natural lymphoid ECM-derived hydrogel. Synthetic extracellular matrix materials may be selected from the group consisting of hydrogels, poly(methyl methacrylate), poly(lactide-co-glycolide), polytetrafluoroethylene, poly(ethylene glycol dimethacrylate) hydrogels (PEGDA or PEGDMA), poly(ethylene oxide), and poly(propylene fumarate-co-ethylene glycol) (PPF-PEG). Natural extracellular matrix (ECM) materials may be selected from the group consisting of collagen, hyaluronic acid hydrogels, calf skin gelatin, fibrinogen, thrombin, and decellularized ECM (such as small intestine submucosa and urinary bladder mucosa).

Each part of the system can be treated separately and then they are combined subsequently to form a bioreactor. In one embodiment, the bioreactor is formed by preparing two multi-well plates, one comprising a first matrix (to be used for the VS) at the bottom of the wells, one comprising a second matrix (to be used for the LTE) at the bottom of the wells. Next, the wells of the first multi-well plate (to be used for the VS) are loaded with blood monocytes and non-monocytic dendritic cell precursors (or any of the other cell types provided above). The blood monocytes and non-monocytic dendritic cell precursors are then stimulated with a test agent or antigen, allowing the stimulated blood monocytes and non-monocytic dendritic cell precursors to convert into mature antigen-presenting cells. The wells of the second multi-well plate (to be used for the LTE) are loaded with a plurality of lymphocytes and leukocytes to prepare the three-dimensional artificial lymphoid tissues. The first multi-well plate (comprising the vaccination sites) is then aligned with the second multi-well plate (comprising the three-dimensional artificial lymphoid tissues) and the wells of one multi-well plate are inserted into the wells of the other multi-well plate to produce multiple bioreactors. The 96-well format can accommodate, e.g., amnion membrane and collagen VS models as well as various LTE designs (e.g., tennis ball model and inverse opal scaffolds).

Example 13

Integrated AIS

Figure 23B:
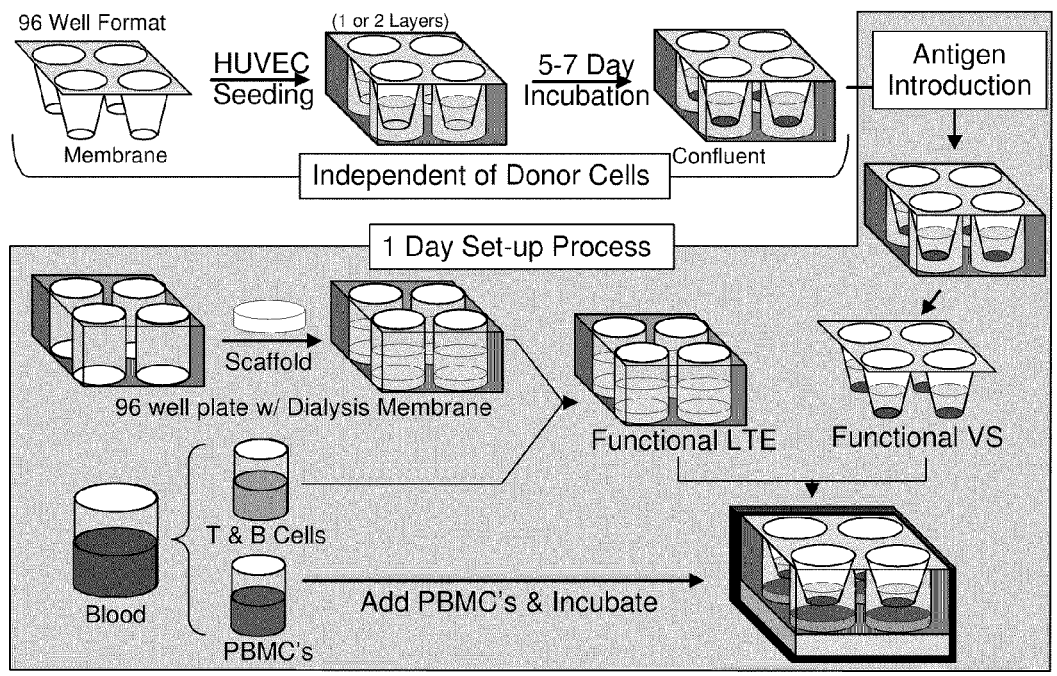

Drawing an analogy with high throughput drug screening technology, an AIS suitable for rapid vaccine or chemical screening can use multiple, low-cost, disposable bioreactors, designed for single-use. Each bioreactor will be challenged with a different antigen and, upon activation of the immune response, harvested for antibodies, B cells, and T cells. In another embodiment of the present invention, an integrated AIS comprises a construct to which PBMCs are added (FIG. 23B). The preparation of the bioreactors are similar to that described for the static model, but in the VS, antigen is attached to or embedded in the membrane before the addition of PBMCs and after the HUVECs have reached confluency.

Example 14

Dialysis Membrane Integration

In further embodiments of the present invention, dialysis membranes can be incorporated in the design of the AIS to reduce the need for media exchanges, which can improve cell viability and improve the detection of low concentration molecules, including proteins and antibodies.

By using dialysis membranes in the LTE (the matrix of the LTE is situated on the dialysis membrane), the incubation well can be designed to allow small molecules to pass freely across the membrane while larger molecules, such as proteins, antibodies, and cytokines, can be retained. The permeability to small molecules provides a means of removing cellular waste, thereby keeping cells viable for longer periods, while the retention of large molecules in each of the localized wells can increase the probability of cytokine or antibody detection.

Cell viability. Assessment of the ability of dialysis membranes to increase cell viability was conducted by preparing cell cultures with and without a dialysis membrane. Cultures of 1 million PBMCs were added to 500 µl of media and were stimulated with PMA and PHA. Each culture was then placed in either a normal 96-well plate or in a dialysis membrane holder (with 3.5 kDa cut off cellulose membrane) suspended in an additional 5 mL of media. A comparison well with 1 million PBMCs in 5.5 mL was prepared as a standard. The cells were then incubated for 3 days at 37° C./5% $CO_2$. After 3 days, the cultures were removed and inspected (visually) for pH changes. The medium in the 'normal' well had turned yellow, indicating acidification and that conditions were not conducive to continued cell growth. The medium in the dialysis membranes-containing culture vessels remained pink, indicating a slightly basic pH, optimal for continued cell growth.

Large molecule retention. Assessment of the ability of dialysis membranes to retain large molecules was conducted by monitoring whether a 50 kDa albumin molecule could permeate across a 10 kDa cut off dialysis membrane. A stock solution of albumin (5 mg/mL) and 1% NaCl was prepared and placed in an open well plate. The 10 kDa dialysis membrane 'bucket' was then suspended in the plate and 500 µl 1% NaCl was added. The well plate was then incubated for 24 hours at 37° C. The plate was then removed and the dialysis well solution was analyzed using a UV-visible spectrophotometer at a wavelength of 278 nm Spectral results and a calibration curves revealed that there was no detectable permeation of the albumin across the dialysis membrane.

Example 15

Microfluidic Bioreactor

In an embodiment of the present invention a "thin-sheet membrane bioreactor" was prepared. This embodiment comprises a microfluidic bioreactor to house an, e.g., ECM-derived membrane as a support scaffold for the vaccination site (VS). In an embodiment of the present invention, the ECM bioreactor, the ECM membrane is held in place by two concentric rings: an inner (e.g., PTFE, Teflon) ring and a larger (e.g., polycarbonate) outer ring. The ECM-derived membrane is sandwiched in the narrow (about 100 µm) gap between the two rings by pressing the inner ring into the outer ring, thereby stretching the ECM-derived membrane tight across the opening in the inner ring. A confluent endothelium can then be grown on either or both sides of the exposed ECM membrane. This approach is readily adaptable to a well-based format. In other embodiments, ported lids and/or retaining rings can be attached independently to either side of the ECM/ring structure, allowing for several different experimental configurations. For example, a ported lid on the top side could provide shear to the endothelium while a retaining ring on the bottom would keep the endothelium in a static condition. The lids can be transparent, allowing microscopic inspection of the vaccination site.

Figure 24:
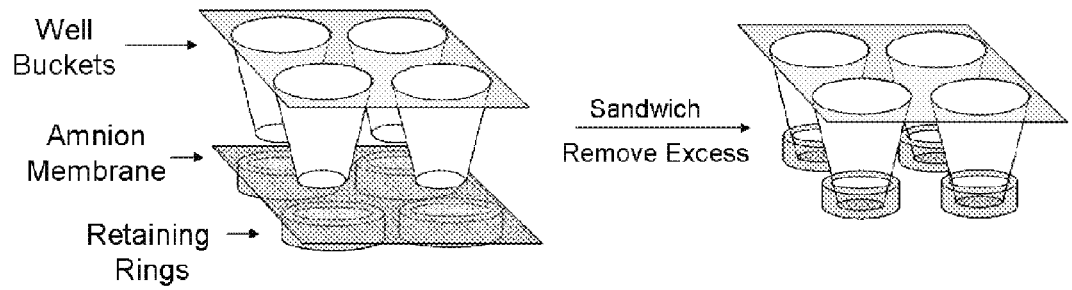
FIG. 24 illustrates a method of mounting an ECM membrane using concentric rings that can be used in a well-based format.

ECM membrane for the VS in a well-based format. In this embodiment of the present invention, the method of mounting the ECM membrane using concentric rings, described previously, can be used in a well-based format, as shown in FIG. 24. Here, the inner Teflon ring is replaced with conventional well buckets that have no floor. The ECM is placed between the buckets and outer retaining rings and the buckets are pressed into the retaining rings (which have a slightly larger diameter than the bottom of the buckets), thereby sandwiching the ECM membrane in place. Excess ECM membrane can then be removed, leaving a tightly stretched membrane across the bottom of the bucket on which to grow the cells of the VS. The buckets can be placed in well plates containing media for cell culture.

Figure 25:
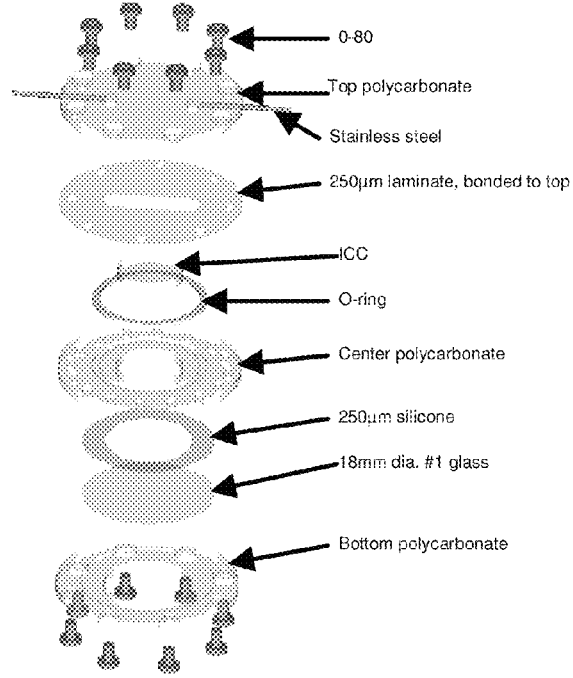
FIG. 25 illustrates a bioreactor.
Figure 25:
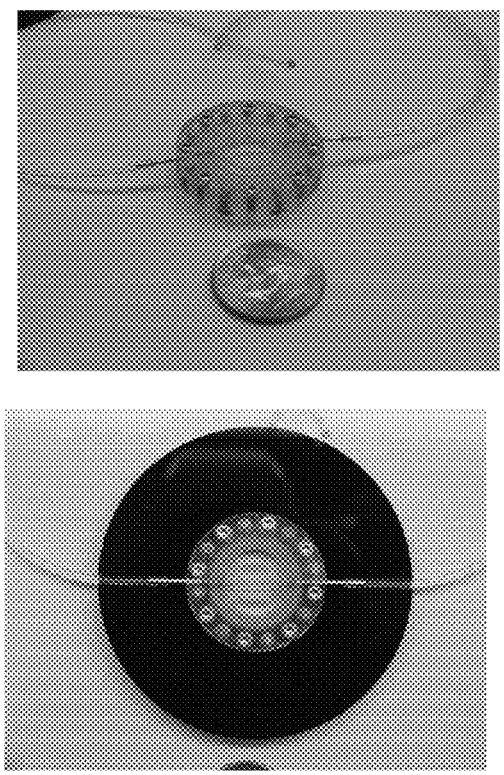

Scaffold Bioreactor. In another embodiment of the present invention, the microfluidic bioreactor described is modified to house a scaffold. An embodiment of the present invention, the ICC bioreactor, is illustrated in FIG. 25. The design enables ease of assembly and robust sealing. As an example, it houses a 9 mm diameter, 1/16"-thick ICC scaffold. Flow can be applied to one side of the scaffold through a ported window and confined to a thin (250 µm) chamber. The other side of the scaffold is mounted against a thin glass cover slip to allow high resolution microscopic examination. A microscope adapter plate (lower right figure) was also fabricated.

Example 16

Integration of Scaffolds in a 96-Well Format

In this embodiment, tissue scaffolds for the LTE or VS have been integrated in a 96-well format.

Figure 26A:
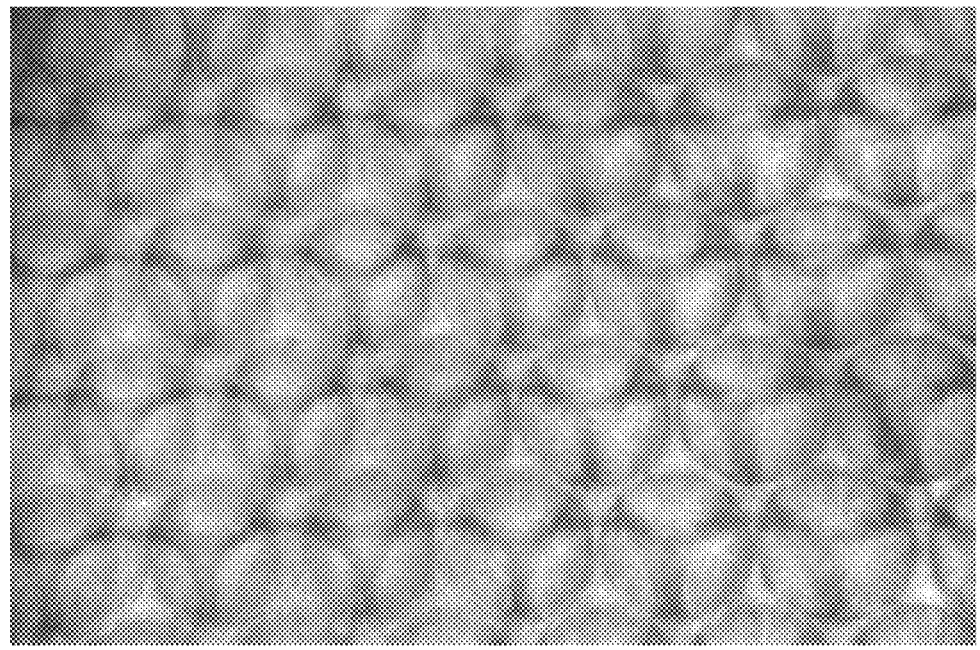

FIG. 26A, first image, magnification ~×20. An ICC scaffold is placed in a well of the 96-well plate, in 500 µl water; bottom view (invertoscope), but other scaffolds can be used, including collagen and microcarriers.

Figure 26B:

FIG. 26B, second image. Top view: well "B" contains 500 µl water; well "C" contains an ICC scaffold in 500 µl water. In this example, the scaffolds are ~7 mm across, ~200 µm thick. The cavities are ~40 µm.

Example 17

Well-Based Format of VS and LTE Integration

Figure 27:
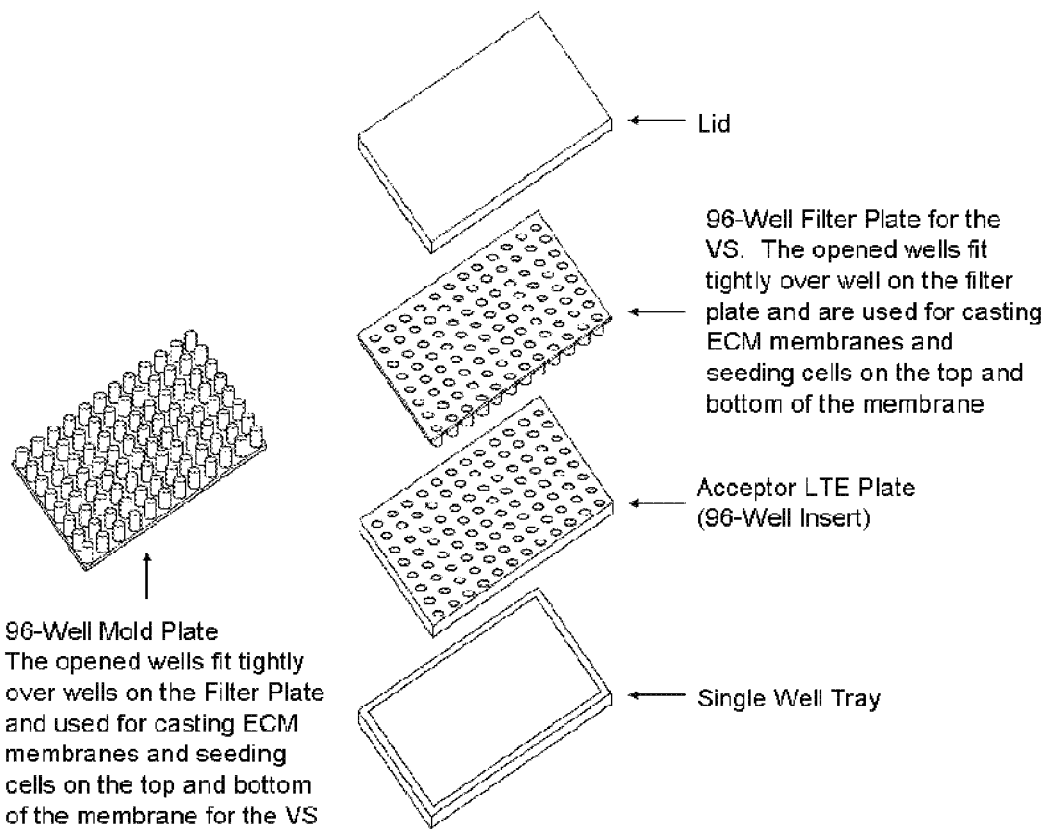
FIG. 27 shows how the VS and LTE constructs can be integrated into a well-based format in which the VS is used in a filter plate and the LTE is placed into the acceptor wells. The VS fits over the LTE in the design illustrated.

In this embodiment, a well-based AIS is designed to be used as an in vitro screening model for, e.g., toxins, pathogens, vaccines, and drug evaluations. FIG. 27 shows how the VS and LTE constructs can be integrated into a well-based format in which the VS is used in a filter plate and the LTE is placed into the acceptor wells. The VS fits over the LTE in the design illustrated.

Example 18

High-Throughput Testing

Figure 28:
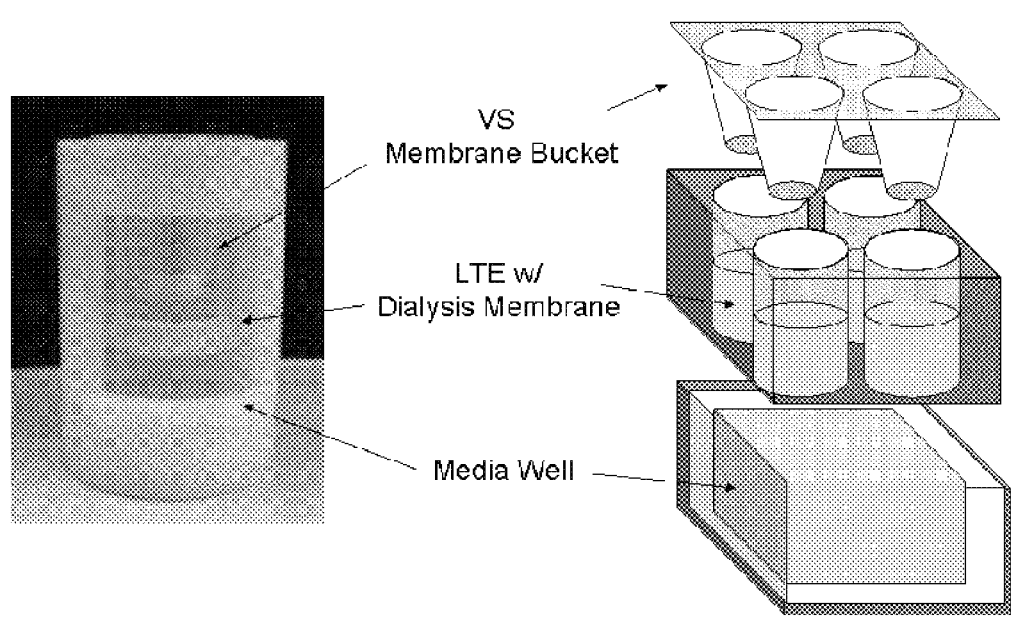
FIG. 28. High throughput testing using the integrated AIS can be accomplished using a static 96-well format, illustrated in this figure. The AIS of this embodiment comprises two parts, the VS and LTE. Each part is prepared separately and combined in the final step of testing. The simplicity of the system facilitates automation. Furthermore, the 96-well format, or other well-based formats, typically used in laboratory automation can accommodate these embodiments of the AIS.

High-throughput testing using the static or integrated AIS (see Examples 12 and 13) can be accomplished using a multi-well format, illustrated in FIG. 28. The AIS in this embodiment comprises two parts, the VS and LTE. Each part is prepared separately and combined in the final step of testing, as in Examples 12 and 13. Following stimulation by the mature antigen-presenting cells, a response from said plurality of lymphocytes is determined The simplicity of the system enables automation. Furthermore, the 96-well format, or other well-based format, typically used in laboratory automation can accommodate these embodiments of the AIS.

Example 19

Preparation of Tissue Constructs

Figure 29:
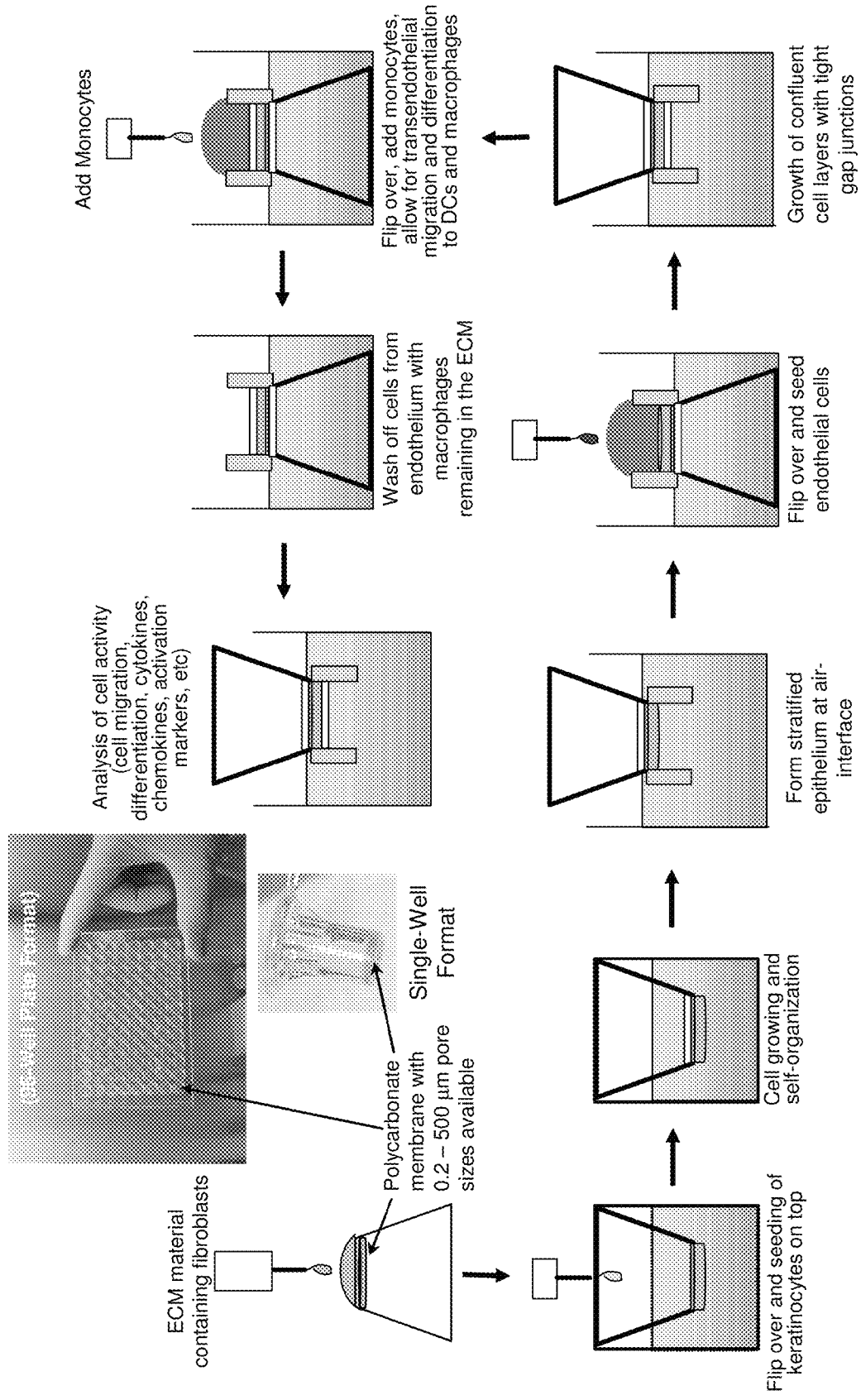
FIG. 29. A representation of a VS model that can be used as a skin equivalent and how it can be tested with an allergen.

Preparation of heterogeneous tissue constructs with the addition of cells on the top and bottom of the tissue construct to create endothelium and epithelium. A representation of the development of the VS model used as a skin equivalent and how it can be tested with an allergen is shown FIG. 29. In this embodiment, a polycarbonate membrane support structure is used to prepare a 3D ECM membrane comprising collagen, other natural polymers, or synthetic materials such as hydrogels, or combinations thereof.

Once an ECM is established that can structurally support two cell layers, a layer of epithelial cells, such as human keratinocytes, can be grown on one side of the matrix. After the keratinocytes have established and begin to form stratified layers, the cells are exposed to an air interface for continued stratification and formation of tight cell junctions. Once a keratinized cell layer is formed, the construct is inverted and a layer of endothelial cells, such as HUVECs, can be grown on the other side.

Once the endothelial cell layer is established, the construct can be inverted again to reinstate the air interface for the keratinocytes. Once the endothelial cells form a confluent monolayer, the tissue construct is complete and ready for characterization and testing of, e.g., chemicals, cosmetics, adjuvants, antigens, and/or inflammatory signals.

Example 20

Introduction of Other Cells

Figure 30:
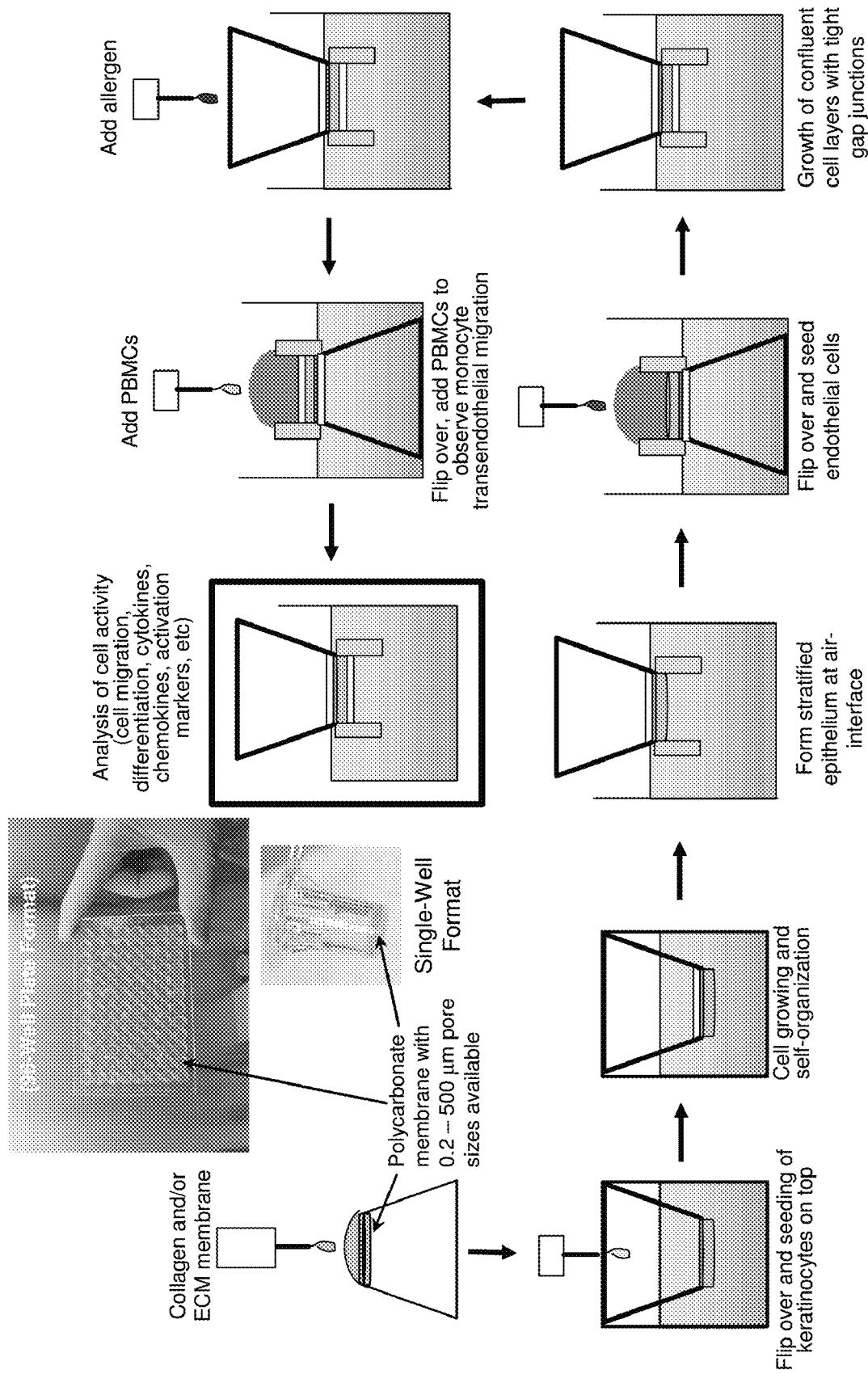
FIG. 30. Introduction of ancillary cells into a 3D construct.

Introduction of ancillary cells inside the 3D construct (FIG. 30). In embodiments of the present invention, fibroblasts or other ancillary cells can be added. Fibroblasts can be mixed with the ECM material before it is added to the membrane support and before the growth of epithelial and/or endothelial cells on the matrix. In embodiments of the VS, purified monocytes can be added to the endothelium; the cells can then transmigrate into the construct. After the monocytes have differentiated to either DCs and reverse-transmigrated from the construct or to macrophages and remained in the construct, remaining cells can be removed from the surface of the endothelium, and the resident macrophages will remain within the construct.

The above description and examples are for the purpose of teaching the person of ordinary skill in the art how to practice the present invention, and it is not intended to detail all those obvious modifications and variations of it that will become apparent to the skilled worker upon reading the description. It is intended, however, that all such obvious modifications and variations be included within the scope of the present invention, which is defined by the following claims. The claims are intended to cover the claimed components and steps in any sequence that is effective to meet the objectives there intended, unless the context specifically indicates the contrary.

What is claimed is:

1. A method for simultaneously producing a plurality of populations of antibodies having different binding specificities, the method comprising:
    (a) preparing a plurality of populations of dendritic cells, wherein each population of dendritic cells is matured in a separate culture in the presence of a different exogenous antigen, comprising adding peripheral blood mononuclear cells (PBMCs) to a plurality of separate vaccination site (VS) cultures, wherein the VS cultures are organized in a first multi-well format, wherein each of the VS cultures comprises a first substantially planar matrix, a plurality of cells consisting of endothelial cells and/or epithelial cells attached to the first matrix and an exogenous antigen of interest, wherein the exogenous antigen of interest differs between each VS culture, under conditions promoting maturation of dendritic cell precursors present in the population of PBMCs to dendritic cells; and
    (b) transferring each population of dendritic cells of (a) to separate three-dimensional artificial lymphoid tissue equivalent (LTE) cultures, wherein the LTE cultures are organized in a second multi-well format, wherein each of the LTE cultures comprises a second matrix and a plurality of lymphocytes attached to the second matrix, under conditions promoting production of antibodies by the lymphocytes, thereby simultaneously producing a plurality of populations of antibodies having different binding specificities.

2. The method of claim 1, wherein said plurality of cells forms an endothelial layer, a vascular endothelial layer, an endothelium or a vascular endothelium on one side of said first matrix.

3. The method of claim 1, wherein said plurality of cells forms an endothelial layer, a vascular endothelial layer, an endothelium or a vascular endothelium on both sides of said first matrix.

4. The method of claim 1, wherein said plurality of cells forms an endothelial layer on one side of said first matrix and an epithelial layer on the other side of said first matrix.

5. The method of claim 1, wherein said plurality of cells forms an endothelial layer on one side of said first matrix and an epithelium on the other side of said first matrix.

6. The method of claim 1, wherein said plurality of cells forms an endothelium on one side of said first matrix and an epithelium on the other side of said first matrix.

7. The method of claim 1, wherein said plurality of cells forms a vascular endothelium on one side of said first matrix and an epithelial layer on the other side of said first matrix.

8. The method of claim 1, wherein said plurality of cells forms an endothelium on one side of said first matrix and an epithelial layer on the other side of said first matrix.

9. The method of claim 1, wherein said plurality of cells forms a vascular endothelium on one side of said first matrix and an epithelium on the other side of said first matrix.

10. The method of claim 1, wherein said plurality of cells forms a vascular endothelial layer on one side of said first matrix and a lymphatic endothelial layer on the other side of said first matrix.

11. The method of claim 1, wherein said plurality of cells forms a vascular endothelium on one side of said first matrix and a lymphatic endothelium on the other side of said first matrix.

12. The method of claim 1, wherein said first matrix comprises a natural biopolymer.

13. The method of claim 12, wherein said natural biopolymer is selected from the group consisting of xenographic extracellular matrix (ECM) sheet, reconstituted collagen matrix, and chitosan/collagen membrane scaffolds.

14. The method of claim 1, wherein said first matrix comprises the natural biopolymer bovine type I collagen on a nylon mesh.

15. The method of claim 1, wherein said first matrix comprises the natural biopolymer bovine type I collagen on a polycarbonate mesh.

16. The method of claim 1, wherein said second matrix comprises synthetic extracellular matrix (ECM) materials.

17. The method of claim 1, wherein said second matrix comprises synthetic extracellular matrix materials selected from the group consisting of hydrogels, poly(methyl methacrylate), poly(lactide-co-glycolide), polytetrafluoroethylene, poly(ethylene glycol dimethacrylate) hydrogels (PEGDA or PEGDMA), poly(ethylene oxide), and poly(propylene fumarate-co-ethylene glycol) (PPF-PEG).

18. The method of claim 1, wherein said second matrix comprises natural ECM material.

19. The method of claim 1, wherein said second matrix comprises a natural ECM material selected from the group consisting of collagen, hyaluronic acid hydrogels, calf skin gelatin, fibrinogen, thrombin, and decellularized ECM.

20. The method of claim 1, wherein said plurality of cells in said vaccination site cultures comprises human cells.

21. The method of claim 1, wherein said plurality of cells in said vaccination site cultures comprise human vascular endothelial cells (HUVECs).

22. The method of claim 1, wherein said plurality of cells in said vaccination site cultures comprise blood vessel endothelial cells.

23. The method of claim 1, wherein said plurality of lymphocytes comprises T cells and B cells.

24. The method of claim 1, wherein said plurality of lymphocytes comprises dendritic cells.

25. The method of claim 1, wherein said plurality of lymphocytes comprises naive T cells and naive B cells.

26. The method of claim 1, wherein said plurality of lymphocytes comprises memory T cells and memory B cells.

27. The method of claim 1, wherein the exogenous antigen of interest is attached to the first matrix.

28. The method of claim 1, wherein the exogenous antigen of interest is embedded in the first matrix.

29. The method of claim 1, wherein each of said vaccination site cultures comprises:
- a first substantially planar matrix comprising an ECM membrane;
- a layer of epithelial cells attached to a first side of the ECM membrane; and
- a layer of endothelial cells attached to a second side of the ECM membrane.

30. The method of claim 1, further comprising isolating antibody-producing B cells from individual LTE cultures of (b) and producing hybridomas from the antibody-producing B cells.

31. The method of claim 1, further comprising isolating antibodies produce in the separate LTE cultures.

32. The method of claim 1, wherein the PBMCs in individual VS cultures are from the same donor.

33. The method of claim 1, wherein the PBMCs added to the plurality of separate VS cultures are from the same donor.

34. The method of claim 1, wherein the different exogenous antigens may be different formulations of the same antigen or different portions of the same antigen.

* * * * *